Figures 1A, 1B:
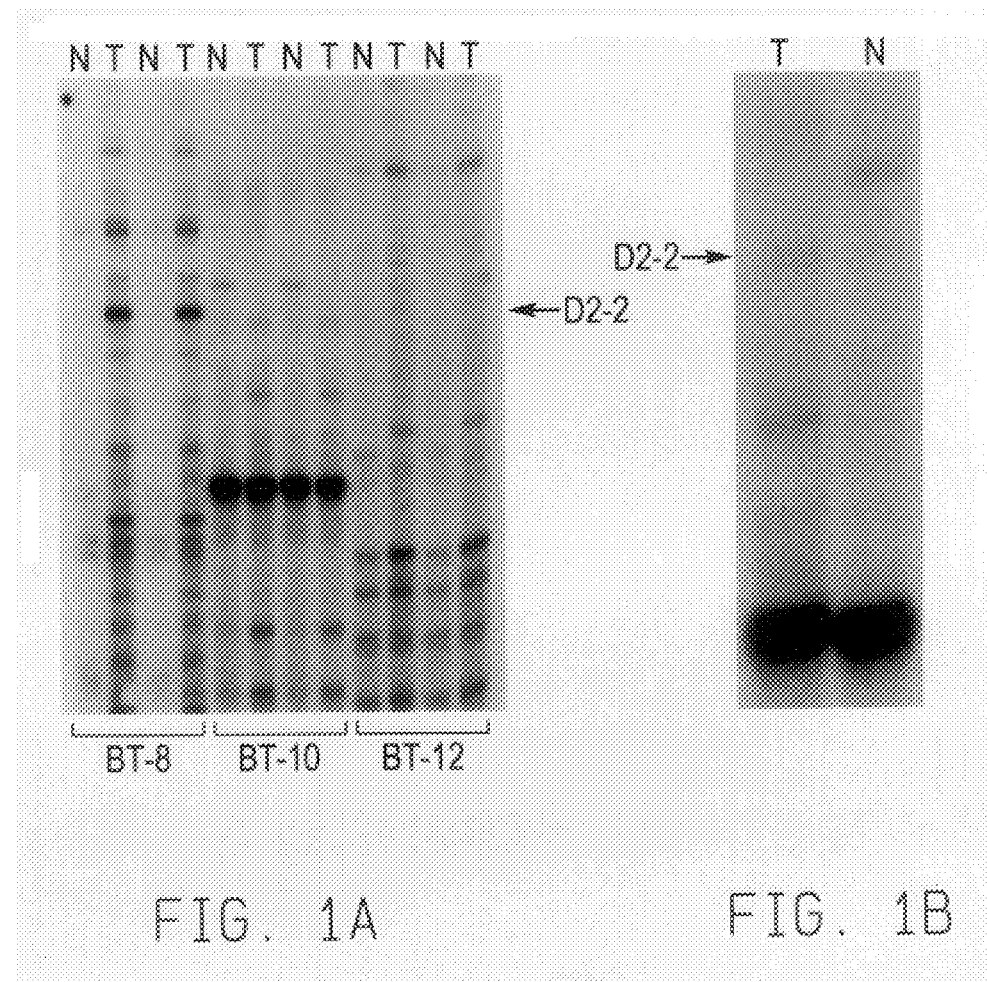

United States Patent [19]

Murphy et al.

[11] Patent Number: 5,874,290
[45] Date of Patent: Feb. 23, 1999

[54] NUCLEOTIDE AND AMINO ACID SEQUENCES OF A D2-2 GENE ASSOCIATED WITH BRAIN TUMORS AND METHODS BASED THEREON

[75] Inventors: Gerald P. Murphy, Seattle; Alton L. Boynton, Redmond; Anil Sehgal, Seattle, all of Wash.

[73] Assignee: Northwest Biotherapeutics, LLC, Seattle, Wash.

[21] Appl. No.: 747,121

[22] Filed: Nov. 8, 1996

[51] Int. Cl.$^6$ ...................................................... C12N 1/20
[52] U.S. Cl. ................................. 435/252.33; 435/252.3; 435/320.1; 514/12; 530/300; 536/23.1; 536/23.5
[58] Field of Search ........................... 435/252.3, 252.33, 435/320.1; 514/12; 530/300; 536/23.1, 23.5

[56] References Cited

PUBLICATIONS

Angel and Karin, 1991, "The Role of Jun, Fos and the AP–1 Complex in Cell–Proliferation and Transformation", Biochem. Biophys. Acta 1072:129–157.
Bauer, D. et al., 1993, "Identification of Differentially Expressed mRNA Species by an Improved Display Technique (DDRT–PCR)", Nucleic Acids Res. 21:4272–4280.
Bogler, O. et al., 1995, "The p53 Gene and Its Role in Human Brain Tumors", Glia 15:308–327.
Chen, J. et al., 1995, "Effects of the MYC Oncogene Antagonists, MAD, on Proliferation, Cell Cycling and the Malignant Phenotype of Human Brain Tumour Cells", Nature Med. 1;638–643.
Eibl, R. et al., 1995, "Expression of Variant CD44 Epitopes in Human Astrocytic Brain Tumors", J. of Neurooncol. 26:165–170.
Elliot, P.J. et al., 1996, "Intravenous RMP–7 Selectively Increases Uptake of Carboplatin into Rat Brain Tumors", Cancer Res. 56:3998–4005.
Faillot, T. et al., 1996, "A Phase I Study of an Anti–Epidermal Growth Factor Receptor Monoclonal Antibody for the Treatment of Malignant Gliomas", Neurosurgery 39:478–483.
Fanger and Drakeman, 1995, "By Combining the Well–Known Specificity of Monoclonal Antibodies with New Insights into How the Immune System is Triggered, Bispecifics May Become Highly Promising Therapeutic Products Offering a Very Efficient and Well–Tolerated Approach to the Immunotherapy of Life–Threatening Diseases", DN&P 3:133–137.

Furnari, F. et al., 1995, "Genetics and Malignant Progression of Human Brain Tumours", Cancer Surv. 25:233–275.
Hadman, M. et al. 1995, "Modifications to the Differential Display Technique Reduce Background and Increase Sensitivity", Anal. Biochem. 226:383–386.
Ikonomov, O. et al., 1996, "Differential Display Protocol with Selected Primers that Preferentially Isolates mRNAs of Moderate– to Low–Abundance in a Microscopic System", Biotechniques 20:1030–1042.
Jung, J. et al., 1995, "Increased Levels of p21$^{WAF1/Cip1}$ in Human Brain Tumors", Oncogene 11:2021–2028.
Laws and Thapar, 1993, "Brian Tumors", CA Cancer J. Clin. 43:263–271.
Liang, P. et al., 1992, "Differential Display and Cloning of Messenger RNAs from Human Breast Cancer versus Mammary Epithelial Cells", Cancer Res. 52:6966–6968.
Liang and Pardee, 1992, "Differential Display of Eukaryotic Messenger RNA by Means of the Polymerase Chain Reaction", Science 257:967–971.
Parker, S. et al., 1996, "Cancer Statistics", CA Cancer J. Clin. 46:5–28.
Previtali, S. et al., 1996, "$\alpha 6\beta 4$ and $\alpha 6\beta 1$ Integrins in Astrocytomas and Other CNS Tumors", Neuropathol. Exp. Neurol. 55:456–465.
Takano, S. et al., 1996, "Concentration of Vascular Endothelial Growth Factor in the Serum and Tumor Tissue of Brain Tumor Patients", Cancer Res. 56:2185–2190.
Tsuzuki, T. et al., 1996, "Alterations of Retinoblastoma, p53, p16(CDKN2), and p15 Genes in Human Astrocytomas", Cancer 78:287–293.
Yamamoto, M. et al., 1996, "Differential Expression of Membrane–Type Matrix Metalloproteinase and Its Correlation with Gelatinase A Activation in Human Malignant Brain Tumors in Vivo and in Vitro" Cancer Res. 56:384–392.

*Primary Examiner*—Charles L. Patterson, Jr.
*Assistant Examiner*—Nashaat T. Nashed
*Attorney, Agent, or Firm*—Pennie & Edmonds

[57] ABSTRACT

Nucleotide sequences of D2-2 genes (human D2-2 and D2-2 homologs of other species), and amino acid sequences of their encoded proteins, as well as derivatives (e.g., fragments) and analogs thereof are disclosed. Nucleic acids hybridizable to or complementary to the nucleotide sequences are also disclosed. D2-2 is a gene expressed at high levels in glioblastoma multiforme tissue as well as certain other forms of tumors and cancers. Therapeutic and diagnostic methods and compositions based on D2-2 proteins fragments and analogs, anti-D2-2 antibodies and nucleic acids for treatment of disorders of overproliferation (e.g., tumors, cancer and hyperproliferative disorders are disclosed.

16 Claims, 13 Drawing Sheets

```
TGC AGG AAT TCG GCA CGA GGA TTG AGT AAC TTG CTG TCA CTG CTT GTA
 C   R   N   S   A   R   G │ L   S   N   L   L   S   L   L   V │
                           8                                  16

CTT TGT AGA CAG CCT GAG AGT GGC AGG ACC│TTA TGT GAA TGG GGG GGA
 L   C   R   Q   P   E   S   G   R   T │ L   C   E   W   G   G
                                        27

TGG ACT GTG│ATC AGT GCC GGG GAG TCT CTG AAG CTG GGG TCC CCA CCT
 W   T   V │ I   S   A   G   E   S   L   K   L   G   S   P   P
           35

CCA GGG GCT TCT GCT CAG AGG│TTA CGT GTG CAG TTT GAA GAT GTA│CAT
 P   G   A   S   A   Q   R │ L   R   V   Q   F   E   D   V │ H
                           56                              63

CTT GAC CTC CGG TTT AGA GGC ACT TTC TGC CCA TCA GAT TCC AAA CTC T
 L   D   L   R   F   R   G   T   F   C   P   S   D   S   K   L

AGGGGGGCAG CACCTTTTCT TTGCTCCCAA ACACCAACCA ACACCCCTTC ACAGGACCAG
CACTGTTAGG ATGGCTAAGT GGATGTTTTA TGTTCCCACG TCCCTGACTC TGTTTCAGAG
GTTGTGTCTG CTCTCCCAGC CCCTGAAGCC AAAATGACTT CCTGCAGCTT TCATGAGCTC
AGCCTCTTCC CTGGGGTATG TGTGAGGGGG AAAGCCTGGT TCAAGTTTAG ATTTATTTCT
AGGGAGCCCT GGTTTCTTCA TACCAGAGGC ACTTTGGAGT GGGGTATCTT
```

FIG. 3A

```
TTTTTCATTT GTTTTTTGA  TACAGAGTCT CGCTCTATTG CCCAGGCTGG AGTGCGGTGG
CACAATCTCA GCTTACTGCA ACCTCCACCT CCAGGGTTCA AGCGATTCTC CTGCCTCAGC
CTCCCGAGTA GCTGGCATTA CAGGCACCTG CCACCACACC CGGCTAAATT TTGTATTTTT
AGTAGAGAAG GGGTTTCACC ATGTTGGTGA GGCTTGTCTC AAACTGACTT CAAGTGATCC
ACTTGCTTCG GCCTCCCAAA GTGCTGGGAT TACAGGCGTG AGCCATCACG CCCAGCCGAG
GGTATCTTTT ATACCAACAA ATTAGATGAC TGAGGTGTAA TGGACAAATC CTATGCACAA
AGTGAGGGTA TCTGAATATG TGGGCGGGAG TCAAAAATTT TTAGCTACTT TAACACTAAA
GTCAAACTAA AGTAGCTTCA AAAAGACTTC TCAAGATGCA GTATGGCCTG CTGAGGTTTT
TTTGTTTTTT TTTTTTTTAA GACAGAGAGT CGCTCGTCGC CCAGGCCGCA GTGCAGTAGC
ATGATCTCAG CTCACTGCAA CCTCCACCTC CCGGGTTCAA GCGATTCTCC TGTCTCAGCC
TCCTAAGTAG CTGGGACTAC AGGCACCTGC CACCACGCCC ATCTAAGTTT TGCATTTTTA
GTAGCGACGG TTTCACCTTG TTGCCCAGGC TGGTTTTGTT GGCCAATTGT CTCTAAACTG
CTGTCAAAAA AAGGAATGGA TCAGATTGTC TTGAATAGGG CAGAGCTAAC CTGTAATCAC
CTGTGTGATG AGAAACAGCT TTGACTGCAT TTTACTCCTG ACCTGGCCTA AGCTTTCTGT
TTACATAAGA TTTTCAAGA  ATTCAACTTC AAGTAGCAGC CGAGAGAGCT GCCTCAGGAT
TCTCTCAAAA ACTGGGAATA ATATGGGAAC ATTTGTTTCT TCTAAAAATA AGGCAAATGT
TACATTGAAT GATTGGGGGG GTGAGGTTTA ATTGGAAATG GTCTCTGGGG ACTGAAAACT
GATGTTTTTG CAGATTACCT CAGGGAAACG GAGGTTTGTT GAGTTTACAG ACACATTAAA
CCAAAGGCCG TGGGAAAACC CCTCTCCAGC TCCAGGGGAT TGGTCAGGAC CACCCACTAA
CCAGTGCCTT CCTTCTTAAC ATTCACTTTT AGCAGCTTGT GTTTATTTTA CATGGGCAGT
TTTGATGGGA AATTGCCATG ACCACAGGGG TTTGGAGTTC TGCTTTTTTT TTTTCTTCTT
CTTTTTCGGG GGACTGGGGG ACTCCTCCCA AGATCACATT TTAGCATCTT TCTCTCCTAC
TCCATTTAGA AAAATAAGTA ACAGGTGAAA TGTGGTCTCA GTGTTAACGG GATAATTCTG
CTACCGGCTC CTCCCTGATG ATTCTGAAAT ACACTACTGA ACGAGCTCTG GCTGGTCCTT
TCAAAAAAAA A
AAAAAAAAA
```

FIG. 3B

D2-2

D1-2

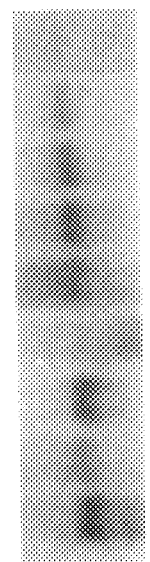

- NORMAL BRAIN
- PROMYELOCYTIC LEUKEMIA HL-60
- HELA CELL S3
- CHRONIC MYELOGENOUS LEUKEMIA K-562
- LYMPHOBLASTIC LEUKEMIA MOLT-4
- BURKITT'S LYMPHOMA RAJI
- COLORECTAL ADRENOCARCINOMA SW480
- LUNG CARCINOMA A549
- MELANOMA G361

↑
D2-2

FIG. 6A

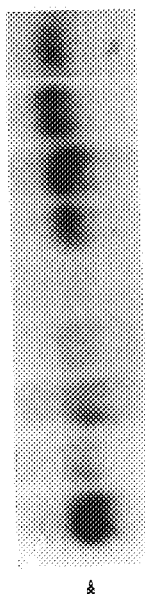

- NORMAL BRAIN
- PROMYELOCYTIC LEUKEMIA HL-60
- HELA CELL S3
- CHRONIC MYELOGENOUS LEUKEMIA K-562
- LYMPHOBLASTIC LEUKEMIA MOLT-4
- BURKITT'S LYMPHOMA RAJI
- COLORECTAL ADRENOCARCINOMA SW480
- LUNG CARCINOMA A549
- MELANOMA G361

↑
β ACTIN

FIG. 6B

☒ ADULT   ☐ FETAL (20 WEEKS)

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 2002 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

| | | | | | | |
|---|---|---|---|---|---|---|
| TGCAGGAATT | CGGCACGAGG | ATTGAGTAAC | TTGCTGTCAC | TGCTTGTACT | TTGTAGACAG | 60 |
| CCTGAGAGTG | GCAGGACCTT | ATGTGAATGG | GGGGGATGGA | CTGTGATCAG | TGCCGGGGAG | 120 |
| TCTCTGAAGC | TGGGGTCCCC | ACCTCCAGGG | GCTTCTGCTC | AGAGGTTACG | TGTGCAGTTT | 180 |
| GAAGATGTAC | ATCTTGACCT | CCGGTTTAGA | GGCACTTTCT | GCCCATCAGA | TTCCAAACTC | 240 |
| TAGGGGCGCA | GCACCTTTTC | TTTGCTCCCA | AACACCAACC | AACACCCCTT | CACAGGACCA | 300 |
| GCACTGTTAG | GATGGCTAAG | TGGATGTTTT | ATGTTCCCAC | GTCCCTGACT | CTGTTTCAGA | 360 |
| GGTTGTGTCT | GCTCTCCCAG | CCCCTGAAGC | CAAAATGACT | TCCTGCAGCT | TTCATGAGCT | 420 |
| CAGCCTCTTC | CCTGGGGTAT | GTGTGAGGGG | GAAAGCCTGG | TTCAAGTTTA | GATTTATTTC | 480 |
| TAGGGAGCCC | TGGTTTCTTC | ATACCAGAGG | CTACCCTTAG | AACTTTGGAG | TGGGGTATCT | 540 |
| TTTTTTCATT | TGTTTTTTTG | ATACAGAGTC | TCGCTCTATT | GCCCAGGCTG | GAGTGCGGTG | 600 |
| GCACAATCTC | AGCTTACTGC | AACCTCCACC | TCCAGGGTTC | AAGCGATTCT | CCTGCCTCAG | 660 |
| CCTCCCGAGT | AGCTGGCATT | ACAGGCACCT | GCCACCACAC | CCGGCTAAAT | TTTGTATTTT | 720 |
| TAGTAGAGAA | GGGGTTTCAC | CATGTTGGTG | AGGCTTGTCT | CAAACTGACT | TCAAGTGATC | 780 |
| CACTTGCTTC | GGCCTCCCAA | AGTGCTGGGA | TTACAGGCGT | GAGCCATCAC | GCCAGCCGA | 840 |
| GGGTATCTTT | TATACCAACA | AATTAGATGA | CTGAGGTGTA | ATGGACAAAT | CCTATGCACA | 900 |

| | | | | | | |
|---|---|---|---|---|---|---|
| AAGTGAGGGT | ATCTGAATAT | GTGGGCGGGA | GTCAAAAATT | TTTAGCTACT | TTAACACTAA | 960 |
| AGTCAAACTA | AAGTAGCTTC | AAAAAGACTT | CTCAAGATGC | AGTATGGCCT | GCTGAGGTTT | 1020 |
| TTTTGTTTTT | TTTTTTTTA | AGACAGAGAG | TCGCTCGTCG | CCCAGGCCGC | AGTGCAGTAG | 1080 |
| CATGATCTCA | GCTCACTGCA | ACCTCCACCT | CCCGGGTTCA | AGCGATTCTC | CTGTCTCAGC | 1140 |
| CTCCTAAGTA | GCTGGGACTA | CAGGCACCTG | CCACCACGCC | CATCTAAGTT | TTGCATTTTT | 1200 |
| AGTAGCGACG | GTTTCACCTT | GTTGGCCAGG | CTGGTTTTGT | TGGCCAATTG | TCTCTAAACT | 1260 |
| GCTGTCAAAA | AAAGGAATGG | ATCAGATTGT | CTTGAATAGG | GCAGAGCTAA | CCTGTAATCA | 1320 |
| CCTGTGTGAT | GAGAAACAGC | TTTGACTGCA | TTTTACTCCT | GACCTGGCCT | AAGCTTTCTG | 1380 |
| TTTACATAAG | ATTTTTCAAG | AATTCAACTT | CAAGTAGCAG | CCGAGAGAGC | TGCCTCAGGA | 1440 |
| TTCTCTCAAA | AACTGGGAAT | AATATGGGAA | CATTTGTTTC | TTCTAAAAAT | AAGGCAAATG | 1500 |
| TTACATTGAA | TGATTTGGGG | GGTGAGGTTT | AATTGGAAAT | GGTCTCTGGG | GACTGAAAAC | 1560 |
| TGATGTTTTT | GCAGATTACC | TCAGGGAAAC | GGAGGTTTGT | TGAGTTTACA | GACACATTAA | 1620 |
| ACCAAAGGCC | GTGGGAAAAC | CCCTCTCCAG | CTCCAGGGGA | TTGGTCAGGA | CCACCCACTA | 1680 |
| ACCAGTGCCT | TCCTTCTTAA | CATTCACTTT | TAGCAGCTTG | TGTTTATTTT | ACATGGGCAG | 1740 |
| TTTTGATGGG | AAATTGCCAT | GACCACAGGG | GTTTGGAGTT | CTGCTTTTTT | TTTTCTTCT | 1800 |
| TCTTTTTCGG | GGGACTGGGG | GACTCCTCCC | AAGATCACAT | TTTAGCATCT | TTCTCTCCTA | 1860 |
| CTCCATTTAG | AAAAATAAGT | AACAGGTGAA | ATGTGGTCTC | AGTGTTAACG | GGATAATTCT | 1920 |
| GCTACCGGCT | CCTCCCTGAT | GATTCTGAAA | TACACTACTG | AACGAGCTCT | GGCTGGTCCT | 1980 |
| TTCAAAAAAA | AAAAAAAAAA | AA | | | | 2002 |

( 2 ) INFORMATION FOR SEQ ID NO:2:

( i ) SEQUENCE CHARACTERISTICS:
        ( A ) LENGTH: 144 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| | | | | | | |
|---|---|---|---|---|---|---|
| TACTCCATTT | AGAAAAATAA | GTAACAGGTG | AAATGTGGTC | TCAGTGTTAA | CGGGATAATT | 60 |
| CTGCTACCGG | CTCCTCCCTG | ATGATTCTGA | AATACACTAC | TGAACGAGCT | CTGGCTGGTC | 120 |
| CTTTCAAAAA | AAAAAAAAAA | AAAA | | | | 144 |

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( A ) NAME/KEY: Modified Base
        ( B ) LOCATION: 1
        ( D ) OTHER INFORMATION: Where N is any nucleotide ( x i ) SEQUENCE DESCRIPTION: SEQ ID NO:3:

| | | |
|---|---|---|
| NTACTGATCC | ATGACA | 16 |

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (ix) FEATURE:
(A) NAME/KEY: Modified Base
(B) LOCATION: 1
(D) OTHER INFORMATION: Where N is any nucleotide (xi) SEQUENCE DESCRIPTION: SEQ ID NO:4:

NGCTGCTCTC ATACT    15

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(A) NAME/KEY: Modified Base
(B) LOCATION: 1
(D) OTHER INFORMATION: Where N is any nucleotide (xi) SEQUENCE DESCRIPTION: SEQ ID NO:5:

NTGATCTAAG GCACATA    17

(2) INFORMATION FOR SEQ ID NO:6:

(i) SEQUENCE CHARACTERISTICS:
(A) LENGTH: 243 base pairs
(B) TYPE: nucleic acid
(C) STRANDEDNESS: single
(D) TOPOLOGY: linear (ix) FEATURE:
(A) NAME/KEY: Coding Sequence
(B) LOCATION: 1...240
(D) OTHER INFORMATION:

(xi) SEQUENCE DESCRIPTION: SEQ ID NO:6:

| TGC | AGG | AAT | TCG | GCA | CGA | GGA | TTG | AGT | AAC | TTG | CTG | TCA | CTG | CTT | GTA | 48 |
| Cys | Arg | Asn | Ser | Ala | Arg | Gly | Leu | Ser | Asn | Leu | Leu | Ser | Leu | Leu | Val | |
| 1 | | | | 5 | | | | | 10 | | | | | 15 | | |

| CTT | TGT | AGA | CAG | CCT | GAG | AGT | GGC | AGG | ACC | TTA | TGT | GAA | TGG | GGG | GGA | 96 |
| Leu | Cys | Arg | Gln | Pro | Glu | Ser | Gly | Arg | Thr | Leu | Cys | Glu | Trp | Gly | Gly | |
| | | | 20 | | | | | 25 | | | | | | 30 | | |

| TGG | ACT | GTG | ATC | AGT | GCC | GGG | GAG | TCT | CTG | AAG | CTG | GGG | TCC | CCA | CCT | 144 |
| Trp | Thr | Val | Ile | Ser | Ala | Gly | Glu | Ser | Leu | Lys | Leu | Gly | Ser | Pro | Pro | |
| | | 35 | | | | | 40 | | | | | 45 | | | | |

| CCA | GGG | GCT | TCT | GCT | CAG | AGG | TTA | CGT | GTG | CAG | TTT | GAA | GAT | GTA | CAT | 192 |
| Pro | Gly | Ala | Ser | Ala | Gln | Arg | Leu | Arg | Val | Gln | Phe | Glu | Asp | Val | His | |
| | 50 | | | | | 55 | | | | | 60 | | | | | |

| CTT | GAC | CTC | CGG | TTT | AGA | GGC | ACT | TTC | TGC | CCA | TCA | GAT | TCC | AAA | CTC | T | 241 |
| Leu | Asp | Leu | Arg | Phe | Arg | Gly | Thr | Phe | Cys | Pro | Ser | Asp | Ser | Lys | Leu | | |
| 65 | | | | | 70 | | | | | 75 | | | | | 80 | | |

AG    243

(2) INFORMATION FOR SEQ ID NO:7:

(i) SEQUENCE CHARACTERISTICS:
(A) LENGTH: 80 amino acids
(B) TYPE: amino acid
(C) STRANDEDNESS: single
(D) TOPOLOGY: linear (ii) MOLECULE TYPE: protein (v) FRAGMENT TYPE: internal ( x i ) SEQUENCE DESCRIPTION: SEQ ID NO:7:

| Cys | Arg | Asn | Ser | Ala | Arg | Gly | Leu | Ser | Asn | Leu | Leu | Ser | Leu | Leu | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Cys | Arg | Gln | Pro | Glu | Ser | Gly | Arg | Thr | Leu | Cys | Glu | Trp | Gly | Gly |
|     |     |     | 20  |     |     |     |     | 25  |     |     |     |     | 30  |     |     |

| Trp | Thr | Val | Ile | Ser | Ala | Gly | Glu | Ser | Leu | Lys | Leu | Gly | Ser | Pro | Pro |
|     |     | 35  |     |     |     |     | 40  |     |     |     |     | 45  |     |     |     |

| Pro | Gly | Ala | Ser | Ala | Gln | Arg | Leu | Arg | Val | Gln | Phe | Glu | Asp | Val | His |
|     |     | 50  |     |     |     | 55  |     |     |     |     | 60  |     |     |     |     |

| Leu | Asp | Leu | Arg | Phe | Arg | Gly | Thr | Phe | Cys | Pro | Ser | Asp | Ser | Lys | Leu |
| 65  |     |     |     |     | 70  |     |     |     | 75  |     |     |     |     |     | 80  |

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CTCAGTGTTA ACGGATAAT                                               19

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 1...243
        ( D ) OTHER INFORMATION:

( x i ) SEQUENCE DESCRIPTION: SEQ ID NO:9:

TGTTGAGAAG AGTACATCTT                                            20

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CGGAGCAATA TGAAATGATC T                                        21

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GCAAATACAG CTCCTATTG                                             19

( 2 ) INFORMATION FOR SEQ ID NO:12:

( i ) SEQUENCE CHARACTERISTICS:
        ( A ) LENGTH: 54 base pairs
        ( B ) TYPE: nucleic acid (C) STRANDEDNESS: single
(D) TOPOLOGY: linear (xi) SEQUENCE DESCRIPTION: SEQ ID NO:12:

CCAAACTGGA CATCAAGGAA TTGCTACACA GAAGAACCAC CATCCAGGAT AGAA                54

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:13:

TAGGCCTGAC TGGCATTGTA TTAGCAAACT CATCACTAGA                                40

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...27
        (D) OTHER INFORMATION:

(xi) SEQUENCE DESCRIPTION: SEQ ID NO:14:

TTG AGT AAC TTG CTG TCA CTG CTT GTA                                        27
Leu Ser Asn Leu Leu Ser Leu Leu Val
 1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:15:

Leu Ser Asn Leu Leu Ser Leu Leu Val
 1               5

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...27
        (D) OTHER INFORMATION:

(xi) SEQUENCE DESCRIPTION: SEQ ID NO:16:

TTA TGT GAA TGG GGG GGA TGG ACT GTG                                        27
Leu Cys Glu Trp Gly Gly Trp Thr Val
 1               5

(2) INFORMATION FOR SEQ ID NO:17:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: protein ( v ) FRAGMENT TYPE: internal ( x i ) SEQUENCE DESCRIPTION: SEQ ID NO:17:

```
Leu Cys Glu Trp Gly Gly Trp Thr Val
 1               5
```

( 2 ) INFORMATION FOR SEQ ID NO:18:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: Genomic DNA ( i x ) FEATURE:
    ( A ) NAME/KEY: Coding Sequence
    ( B ) LOCATION: 1...24
    ( D ) OTHER INFORMATION:

( x i ) SEQUENCE DESCRIPTION: SEQ ID NO:18:

```
TTA CGT GTG CAG TTT GAA GAT GTA                              24
Leu Arg Val Gln Phe Glu Asp Val
 1               5
```

( 2 ) INFORMATION FOR SEQ ID NO:19:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: protein ( v ) FRAGMENT TYPE: internal ( x i ) SEQUENCE DESCRIPTION: SEQ ID NO:19:

```
Leu Arg Val Gln Phe Glu Asp Val
 1               5
```

( 2 ) INFORMATION FOR SEQ ID NO:20:

( i ) SEQUENCE CHARACTERISTICS:
    ( A ) LENGTH: 1000 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

```
TATGGCCTGC TGAGGTTTTT TTGTTTTTTT TTTTTTAAG ACAGAGAGTC GCTCGTCGCC     60
CAGGCCGCAG TGCAGTAGCA TGATCTCAGC TCACTGCAAC CTCCACCTCC CGGGTTCAAG   120
CGATTCTCCT GTCTCAGCCT CCTAAGTAGC TGGGACTACA GGCACCTGCC ACCACGCCCA   180
TCTAAGTTTT GCATTTTTAG TAGCGACGGT TTCACCTTGT TGGCCAGGCT GGTTTTGTTG   240
GCCAATTGTC TCTAAACTGC TGTCAAAAAA AGGAATGGAT CAGATTGTCT TGAATAGGGC   300
AGAGCTAACC TGTAATCACC TGTGTGATGA GAAACAGCTT TGACTGCATT TTACTCCTGA   360
CCTGGCCTAA GCTTTCTGTT TACATAAGAT TTTTCAAGAA TTCAACTTCA AGTAGCAGCC   420
```

-continued

| | | | | | | |
|---|---|---|---|---|---|---|
| GAGAGAGCTG | CCTCAGGATT | CTCTCAAAAA | CTGGGAATAA | TATGGGAACA | TTTGTTTCTT | 480 |
| CTAAAAATAA | GGCAAATGTT | ACATTGAATG | ATTTGGGGGG | TGAGGTTTAA | TTGGAAATGG | 540 |
| TCTCTGGGGA | CTGAAAACTG | ATGTTTTTGC | AGATTACCTC | AGGGAAACGG | AGGTTTGTTG | 600 |
| AGTTTACAGA | CACATTAAAC | CAAAGGCCGT | GGGAAAACCC | CTCTCCAGCT | CCAGGGGATT | 660 |
| GGTCAGGACC | ACCCACTAAC | CAGTGCCTTC | CTTCTTAACA | TTCACTTTTA | GCAGCTTGTG | 720 |
| TTTATTTTAC | ATGGGCAGTT | TTGATGGGAA | ATTGCCATGA | CCACAGGGGT | TTGGAGTTCT | 780 |
| GCTTTTTTTT | TTTCTTCTTC | TTTTTCGGGG | GACTGGGGGA | CTCCTCCCAA | GATCACATTT | 840 |
| TAGCATCTTT | CTCTCCTACT | CCATTTAGAA | AAATAAGTAA | CAGGTGAAAT | GTGGTCTCAG | 900 |
| TGTTAACGGG | ATAATTCTGC | TACCGGCTCC | TCCCTGATGA | TTCTGAAATA | CACTACTGAA | 960 |
| CGAGCTCTGG | CTGGTCCTTT | CAAAAAAAAA | AAAAAAAAAA | | | 1000 |

NUCLEOTIDE AND AMINO ACID SEQUENCES OF A D2-2 GENE ASSOCIATED WITH BRAIN TUMORS AND METHODS BASED THEREON

TABLE OF CONTENTS
1. FIELD OF THE INVENTION
2. BACKGROUND OF THE INVENTION
3. SUMMARY OF THE INVENTION
   3.1. DEFINITIONS AND ABBREVIATIONS
4. DESCRIPTION OF THE FIGURES
5. DETAILED DESCRIPTION OF THE INVENTION
   5.1. ISOLATION OF THE D2-2 GENE
   5.2. EXPRESSION OF THE D2-2 GENE
   5.3. IDENTIFICATION AND PURIFICATION OF THE D2-2 GENE PRODUCTS
   5.4. STRUCTURE OF THE D2-2 GENE AND PROTEIN
      5.4.1. GENETIC ANALYSIS
      5.4.2. PROTEIN ANALYSIS
   5.5. ANTIBODIES AND IMMUNE CELLS TO D2-2
      5.5.1. GENERATION OF ANTIBODIES TO D2-2 PROTEINS AND DERIVATIVES THEREOF
      5.5.2. GENERATION OF ACTIVATED IMMUNE CELLS BY EXPOSURE TO D2-2 PROTEINS OR DERIVATIVES THEREOF
   5.6. D2-2 PROTEINS, DERIVATIVES AND ANALOGS
      5.6.1. DERIVATIVES OF D2-2 CONTAINING ONE OR MORE DOMAINS OF THE PROTEIN
   5.7. ASSAYS OF D2-2 PROTEINS, DERIVATIVES AND ANALOGS
   5.8. DIAGNOSIS AND SCREENING
   5.9. THERAPEUTIC USES
      5.9.1. TREATMENT AND PREVENTION OF DISORDERS INVOLVING OVERPROLIFERATION OF CELLS
         5.9.1.1. MALIGNANCIES
         5.9.1.2. PREMALIGNANT CONDITIONS
         5.9.1.3. GENE THERAPY
      5.9.2. TREATMENT AND PREVENTION OF HYPERPROLIFERATIVE AND DYSPROLIFERATIVE DISORDERS
         5.9.2.1. ANTISENSE REGULATION OF D2-2 EXPRESSION
            5.9.2.1.1 D2-2 ANTISENSE NUCLEIC ACIDS
            5.9.2.1.2. THERAPEUTIC USE OF D2-2 ANTISENSE NUCLEIC ACIDS
   5.10. DEMONSTRATION OF THERAPEUTIC OR PROPHYLACTIC UTILITY
   5.11. THERAPEUTIC/PROPHYLACTIC ADMINISTRATION AND COMPOSITIONS
      5.11.1. TREATMENT AND PREVENTION OF HYPOPROLIFERATIVE DISORDERS
   5.12. ADDITIONAL USE OF INCREASED D2-2 FUNCTION TO PROMOTE INCREASED GROWTH
   5.13. SCREENING FOR D2-2 AGONISTS AND ANTAGONISTS
   5.14. ANIMAL MODELS
6. EXAMPLE
   6.1. MATERIALS AND METHODS
      6.1.1. HUMAN TISSUES AND CELL LINES
      6.1.2. DIFFERENTIAL DISPLAY—POLYMERASE CHAIN REACTION (DD-PCR)
      6.1.3. GENE-SPECIFIC REVERSE TRANSCRIPTION POLYMERASE CHAIN REACTION (RT-PCR)
      6.1.4. CLONING AND SEQUENCING OF D2-2
      6.1.5. NORTHERN BLOT ANALYSIS
      6.1.6. DOT BLOT ANALYSIS
      6.1.7. QUANTITATION OF NORTHERN AND SOUTHERN BLOTS
   6.2. RESULTS
      6.2.1. ISOLATION OF DIFFERENTIALLY EXPRESSED GENES USING DD-PCR
      6.2.2. SEQUENCE ANALYSIS OF CLONE D2-2
      6.2.3. EXPRESSION OF D2-2 IN TUMOR TISSUES
      6.2.4. EXPRESSION OF D2-2 IN BRAIN TUMOR CELL LINES AND NORMAL HUMAN (FETAL) ASTROCYTES
      6.2.5. EXPRESSION OF D2-2 IN HUMAN TUMOR CELL LINES
      6.2.6. EXPRESSION OF D2-2 IN DIFFERENT REGIONS OF NORMAL HUMAN BRAIN
      6.2.7. EXPRESSION OF D2-2 IN NORMAL HUMAN TISSUE
      6.2.8. EXPRESSION OF D2-2 DURING DEVELOPMENT
      6.2.9. EXPRESSION OF D2-2 IN CULTURE MEDIUM CONTAINING OR LACKING SERUM
   6.3. DISCUSSION
7. DEPOSIT OF MICROORGANISM

1. FIELD OF THE INVENTION

The present invention relates to a novel D2-2 gene and its encoded protein product(s), as well as derivatives and analogs thereof. Production of D2-2 proteins, derivatives, and antibodies is also provided. The invention further relates to therapeutic compositions and methods of diagnosis and therapy.

2. BACKGROUND OF THE INVENTION

Brain tumors are among the leading cause of death among young children and adults. A survey by the American Cancer Society has documented that 13,300 people died of brain tumors in 1995 and over 17,900 will die in 1996 (Parker et al., 1996, CA Cancer J. Clin., 46:5–28). The number of deaths due to brain tumors has been increasing at a significant rate each year. On average, 25,000 Americans are diagnosed with brain cancer yearly. Brain tumors claim the lives of more children than any other form of cancer except leukemia.

The increased incidence of brain tumors is not only evident in children but also in adults. It has been documented that a significant increase in mortality has occurred in adult primary malignant tumors between 1982 and 1996 (Parker et al., 1996, CA Cancer J. Clin., 46:5–28). Glioblastomas, astrocytomas and meningiomas are the most common brain tumors that affect adults (Thapar and Laws, 1993, CA Cancer J. Clin., 43:263–271).

Glioblastoma multiforme are high grade astrocytomas that grow very rapidly and contain cells that are very malignant (Thapar and Laws, 1993, CA Cancer J. Clin., 43:263–271). The molecular basis of glioblastoma multiforme occurrence may involve systematic events at the chromosomal level or at a gene expression level. These may include inactivation of tumor suppressor genes, activation of oncogenes or specific translocations at the chromosomal level. Some genetic changes at the chromosomal level and gene expression level have been well documented for other brain tumors (Furnari et al., 1995, Cancer Surv., 25:233–275). For example, it has been documented that loss of tumor suppressor(s) genes at chromosome 10, mutations in p53, or overexpression of epidermal growth factor receptor, may be major events leading to glioblastoma multiforme. A number of other genes such as EGFR, CD44, β4 integrins, membrane-type metalloproteinase (MT-MMP), p21, p16, p15, myc, and VEGF have been shown to be overexpressed in different types of brain tumors (Faillot et al., 1996 Neurosurgery, 39:478–483; Eibl et al., 1995, J. of Neurooncol., 26:165–170; Previtali et al., 1996, Neuropathol. Exp. Neurol. 55:456–465; Yamamoto et al., 1996, Cancer Res., 56:384–392; Jung et al., 1995, Oncogene, 11:2021–2028; Tsuzuki et al., 1996, Cancer, 78:287–293; Chen et al., 1995, Nature Med., 1:638–643; Takano, et al., 1996, Cancer Res., 56:2185–2190; Bogler et al., 1995, Glia, 15:308–327). Other genes such as p53 show mutations in the majority of brain tumors (Bogler et al., supra). How the interplay of one or more of these genes leads to tumorigenesis is not known but most likely multiple steps are required for neoplastic transformation. The exact series of events that lead to initiation or progression of glioblastoma are not known at present and useful markers for early detection of brain tumors are lacking.

Citation of references herein shall not be construed as an admission that such references are prior art to the present invention.

3. SUMMARY OF THE INVENTION

The present invention relates to nucleotide sequences of D2-2 genes (human D2-2 and D2-2 homologs of other species), and amino acid sequences of their encoded proteins, as well as derivatives (e.g., fragments) and analogs thereof. Nucleic acids hybridizable to or complementary to the foregoing nucleotide sequences are also provided. In a specific embodiment, the D2-2 gene is a human gene and the D2-2 protein is a human protein.

D2-2 is a gene provided by the present invention, that is expressed at high levels in glioblastoma multiforme tissue as well as certain others forms of tumors and cancers.

The invention also relates to D2-2 derivatives and analogs that are functionally active, i.e., they are capable of displaying one or more known functional activities associated with a full-length (wild-type) D2-2 protein. Such functional activities include but are not limited to antigenicity [ability to bind (or compete with D2-2 for binding) to an anti-D2-2 antibody], immunogenicity (ability to generate antibody which binds to D2-2), and ability to bind (or compete with D2-2 for binding) to a receptor/ligand for D2-2.

The invention further relates to fragments (and derivatives and analogs thereof) of D2-2 which comprise one or more domains of a D2-2 protein.

Antibodies to D2-2, and to D2-2 derivatives and analogs, are additionally provided.

Methods of production of the D2-2 proteins, derivatives and analogs, e.g., by recombinant means, are also provided.

The present invention also relates to therapeutic and diagnostic methods and compositions based on D2-2 proteins and nucleic acids. Therapeutic compounds of the invention include but are not limited to D2-2 proteins and analogs and derivatives (including fragments) thereof; antibodies thereto; nucleic acids encoding the D2-2 proteins, analogs, or derivatives; and D2-2 antisense nucleic acids.

The invention provides for treatment of disorders of overproliferation (e.g., tumors, cancer and hyperproliferative disorders) by administering compounds that decrease or antagonize (inhibit) D2-2 function (e.g., antibodies, antisense nucleic acids, ribozymes).

The invention also provides methods of treatment of disorders involving deficient cell proliferation (growth) or in which cell proliferation is otherwise desired (e.g., degenerative disorders, growth deficiencies, lesions, physical trauma) by administering compounds that promote D2-2 activity (e.g., an agonist of D2-2; nucleic acids that encode D2-2).

Promoting D2-2 function can also be done to grow larger animals and plants, e.g., those used as food or material sources.

Animal models, diagnostic methods and screening methods for predisposition to disorders, and methods for identification of D2-2 agonists and antagonists, are also provided by the invention.

3.1. DEFINITIONS AND ABBREVIATIONS

As used herein, underscoring or italicizing the name of a gene shall indicate the gene, in contrast to its encoded protein product, which is indicated by the name of the gene in the absence of any underscoring or italicizing. For example, "D2-2"shall mean the D2-2 gene, whereas "D2-2" shall indicate the protein product of the D2-2 gene.

As used herein, the following terms shall have the meanings indicated.

D2-2 nucleotides or coding sequences: DNA sequences encoding D2-2 mRNA transcripts, protein, polypeptide or peptide fragments of D2-2 protein, and D2-2 fusion proteins. D2-2 nucleotide sequences encompass DNA, including genomic DNA (e.g. the D2-2 gene) and cDNA.

D2-2: gene products, e.g., transcripts and the D2-2 protein. Polypeptides or peptide fragments of the protein are referred to as D2-2 polypeptides or D2-2 peptides. Fusions of D2-2 protein, polypeptides, or peptide fragments to an unrelated protein are referred to herein as D2-2 fusion proteins.

As used herein, the following terms shall have the abbreviations indicated.

CD: cytoplasmic domain
DD-PCR: differential display—polymerase chain reaction
ECD: extracellular domain
GMT: glioblastoma multiforme tissue
MTB: multiple tissue blot
MTT: meningioma tumor tissue
NBT: normal brain tissue
ORF: open reading frame
RT-PCR: reverse transcription—polymerase chain reaction
TM: transmembrane domain
UTR: untranslated region
Brain tumor cell lines:
  CCF-STTG1: astrocytoma grade IV
  D283 Med: medulloblastoma
  DBTRG-05MG: glioblastoma multiforme
  Hs 683: glioma
  IMR-32: neuroblastoma
  PFSK-1: primitive neuroectodermal tumor
  SW 1783: astrocytoma grade III

4. DESCRIPTION OF THE FIGS.

The present invention may be understood more fully by reference to the following detailed description of the invention, examples of specific embodiments of the invention and the appended figures in which:

FIGS. 1A–B illustrates identification of differentially expressed genes from glioblastoma multiforme tumor tissue and normal brain tissue using differential display-PCR (DD-PCR). Total RNA from tissue samples (PNCF 014) was isolated using the GITC/CsCl$_2$ method (as described in text Section 6.1.2). DD-PCR was performed with one 3' primer BT-3(2), (5'T(T)18NG3') and three 5' primers (BT-8, 5'NTACTGATCCATGACA3' (SEQ ID NO: 3); BT-10, 5'NGCTGCTCTCATACT3' (SEQ ID NO: 4); and BT-12, 5'NTGATCTAAGGCACATA3' (SEQ ID NO: 5). Shown in FIG. 1A is an autoradiogram of DD-PCR using the specific 5' primers as indicated at the bottom of the figure. Note overexpression of the D2-2 gene in tumor (T) compared to normal (N) brain tissue. FIG. 1B shows a detail of the D2-2 region from FIG. 1A using BT-10 as the primer for PCR. N=normal, T=tumor.

Figure 2A:
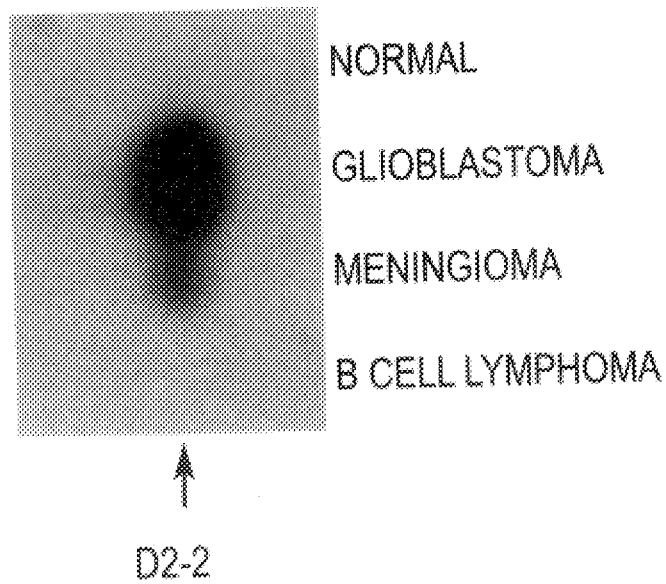
Figure 2B:
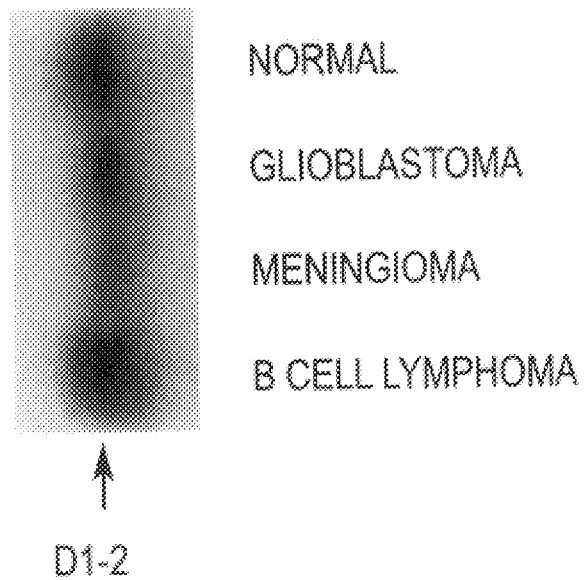
Figure 2C:
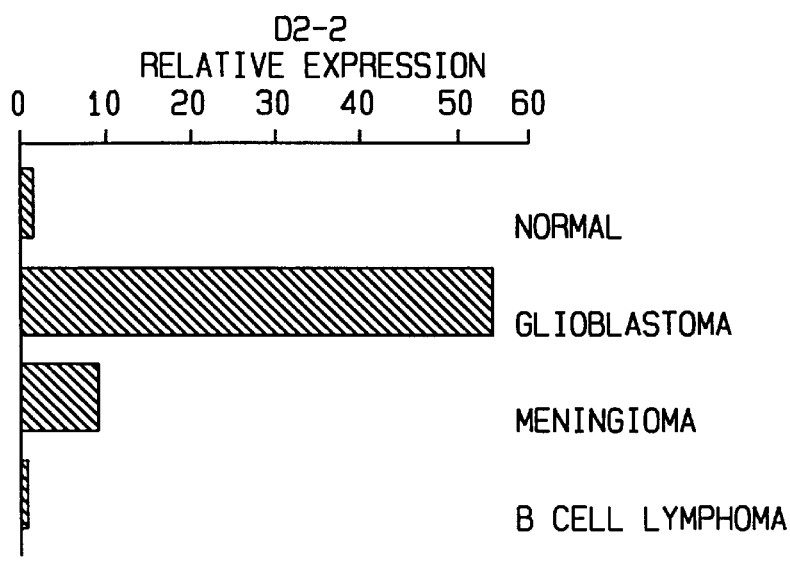

FIGS. 2A–C demonstrates that Clone D2-2 is overexpressed in glioblastoma tumor tissue compared to normal brain, meningioma and B cell lymphoma. FIGS. 2A and 2B are autoradiograms of a RT-PCR for D2-2 (FIG. 2A) and D1-2 (FIG. 2B). FIG. 2C represents the relative expression of D2-2. See text Section 6.1.3. for experimental details.

FIG. 3 shows the partial nucleotide sequence and deduced amino acid sequence of clone D2-2. An EcoRI and XbaI fragment (750 bp) of clone D2-2 was used for screening a human fetal brain library. A 2.0 kb EcoRI-XhoI fragment (SEQ ID NO: 1) was isolated and sequenced to completion by Sequetech (Mountain View, Calif.). The open reading frame is indicated by the deduced amino acid sequence below the nucleotide sequence. A portion (144 bp) (SEQ ID NO: 2) of the original D2-2 fragment sequence (250 bp) isolated by DD-PCR is underlined.

Clone D2-2 contains three nucleotide sequences encoding HLA-A2$^+$ motifs (SEQ ID NO: 14, SEQ ID NO: 16, SEQ ID NO: 18). These sequences are bracketed and overlined. The deduced amino acid sequence for each is indicated below it. Amino acids 8–16 are represented by SEQ ID NO: 15, amino acids 27–35 are represented by SEQ ID NO: 17, and amino acids 56–63 are represented by SEQ ID NO: 19.

Figure 4C:
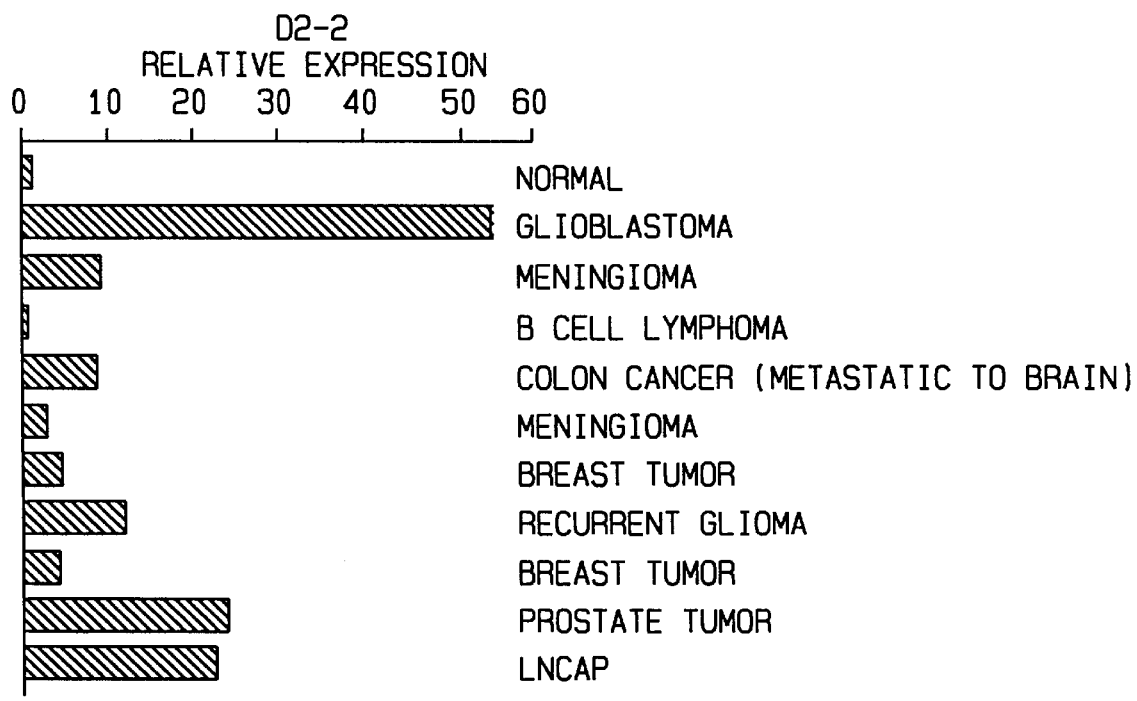
Figure 4A:
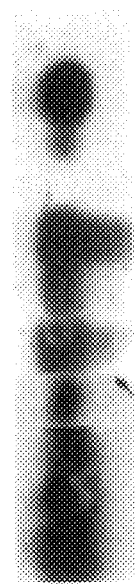
Figure 4B:
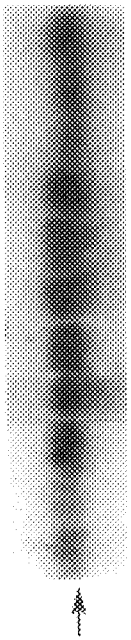

FIGS. 4A–C shows expression of D2-2 in tumor tissues. Total RNA was isolated from several normal and tumor tissues. RT-PCR for D2-2 and D1-2 was performed as described in text Section 6.1.3. FIG. 4A shows D2-2 expression; FIG. 4B shows D1-2 expression. FIG. 4C is a bar graph showing relative expression of D2-2 after correction for gel loading based on D1-2 expression.

Figure 5A:
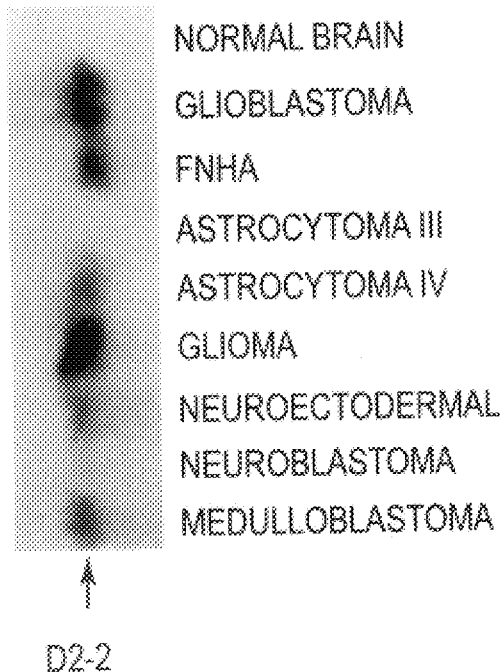
Figure 5B:
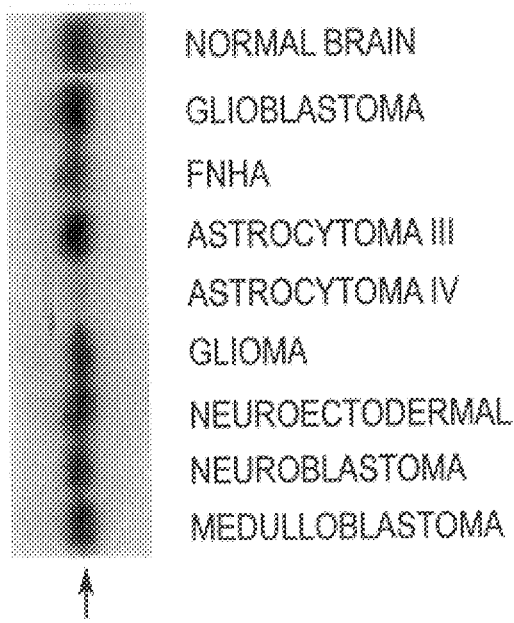
Figure 5C:
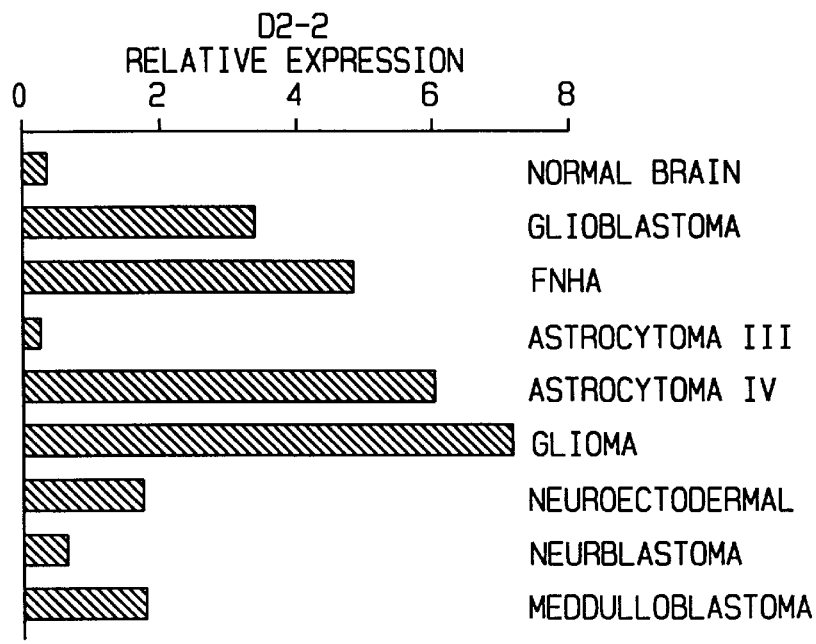

FIGS. 5A–C illustrates expression of D2-2 in brain tumor cell lines and normal fetal human astrocytes. FIGS. 5A–B is an autoradiogram of a Southern blot of D2-2 expression (FIG. 5A) and of D1-2 expression (FIG. 5B) in various brain tumor cell lines and normal fetal human astrocytes. FIG. 5C represents the relative expression of D2-2 in respective cell lines after correction for gel loading based on D1-2 expression.

Figure 6C:
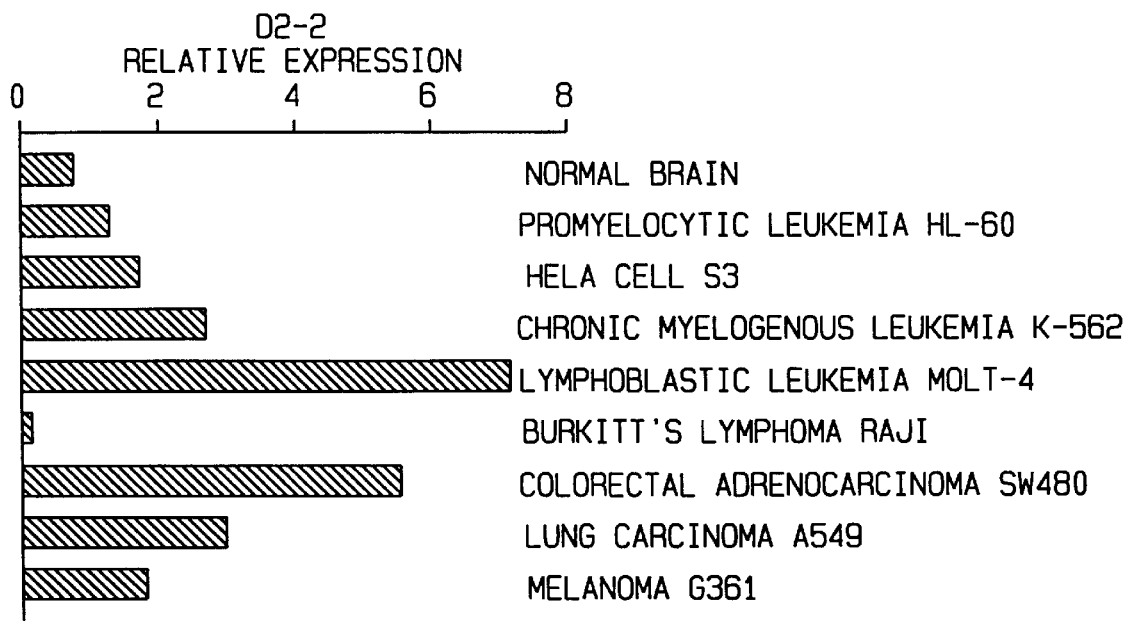

FIGS. 6A–C shows expression of D2-2 in human cancer cell lines. FIGS. 6A–B is an autoradiogram of a Northern blot of D2-2 expression (FIG. 6A) and of β actin expression (FIG. 6B), which serves as an internal control for gel loading in various human cancer cell lines. FIG. 6C is a bar graph of relative expression of D2-2 after correction for gel loading based on β actin expression. See text Section 6.1.5 for experimental details.

Figure 7A:
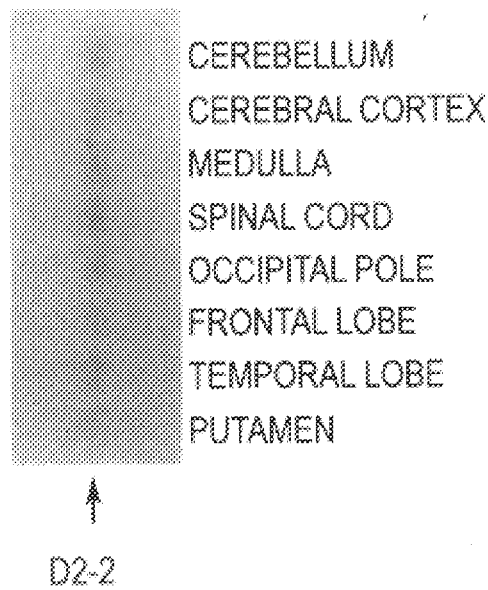
Figure 7B:
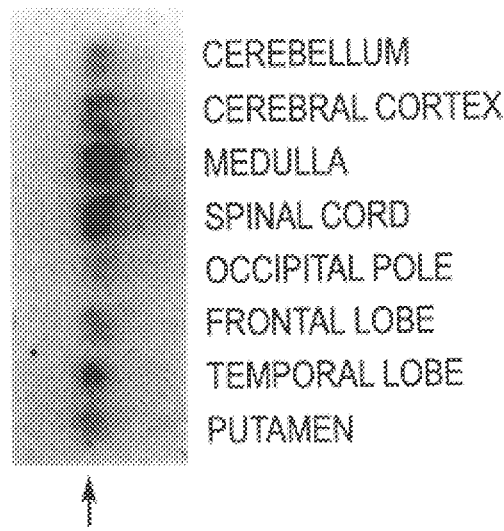
Figure 7C:
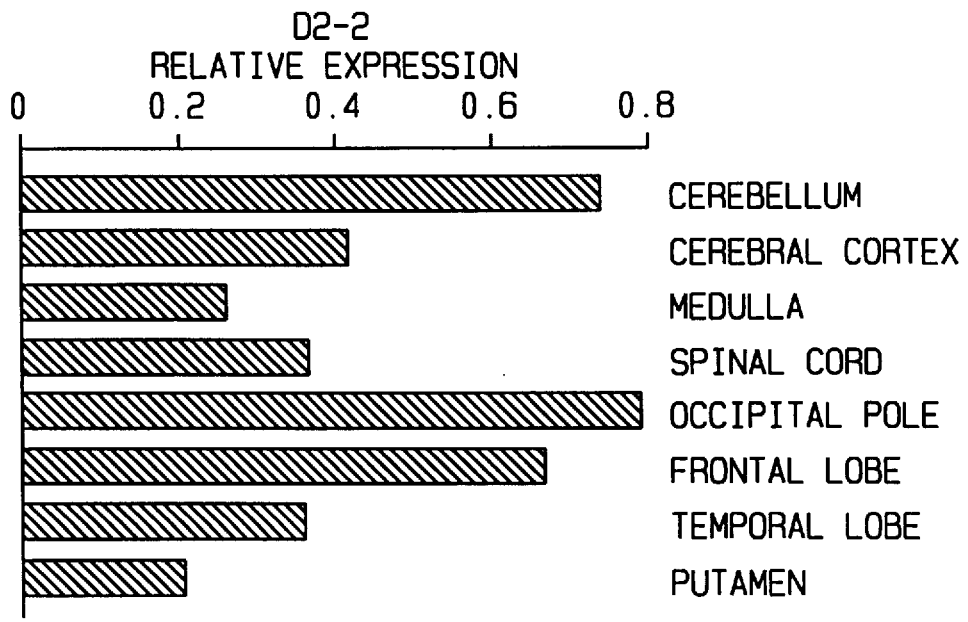

FIGS. 7A–C shows expression of D2-2 in different regions of the brain. FIGS. 7A–B is an autoradiogram of a Northern blot of D2-2 expression (FIG. 7A) and of β actin expression (FIG. 7B), which serves as an internal control for gel loading. FIG. 7C is a bar graph of relative expression of D2-2 after correction for gel loading based on β actin expression. See text Section 6.1.5 for experimental details.

Figures 8A, 8B:
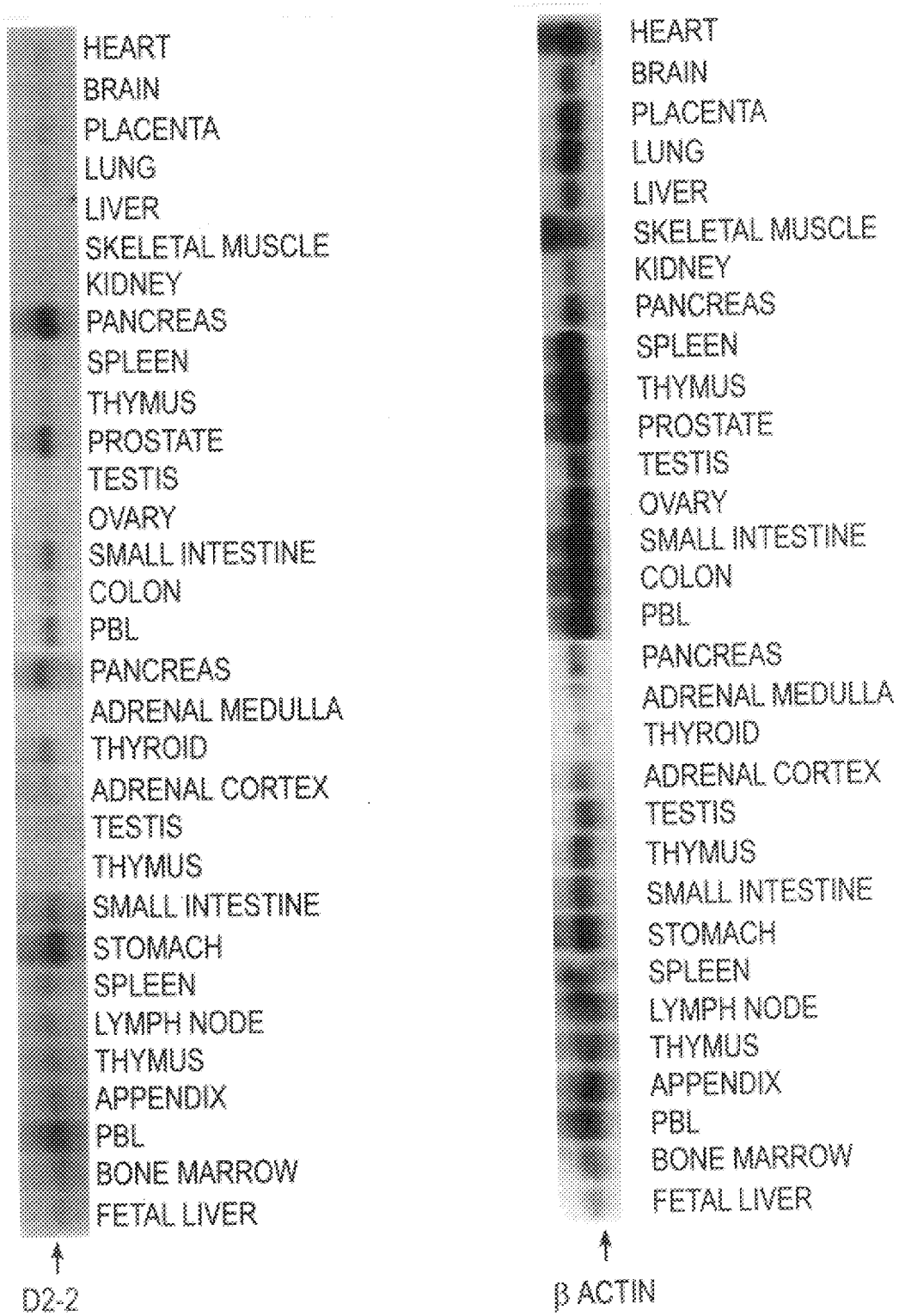
Figure 8C:
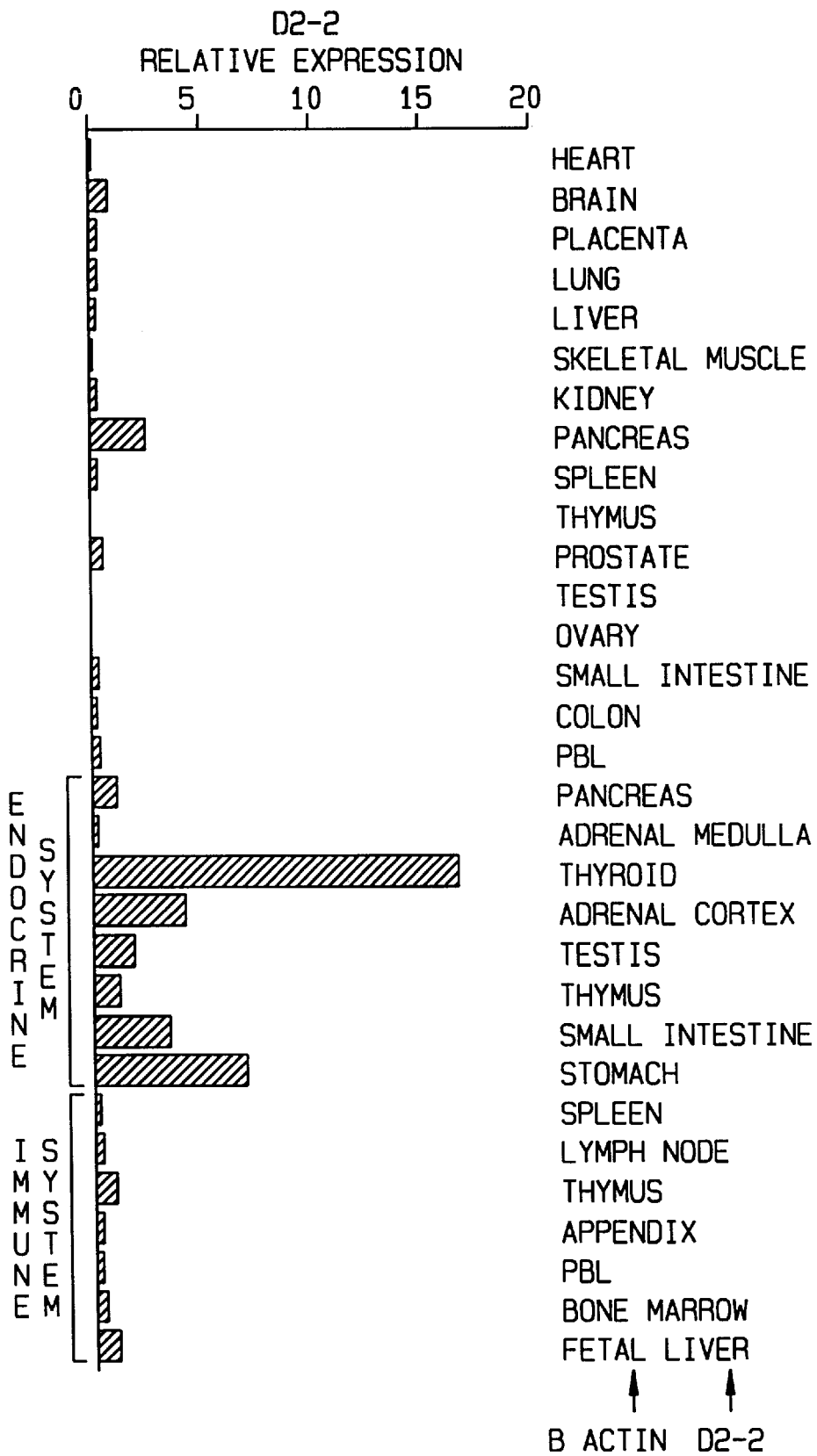

FIGS. 8A–C shows expression of D2-2 in normal human tissues. FIG. 8A-B is an autoradiogram of a Northern blot of D2-2 expression (FIG. 8A) and of β actin expression (FIG. 8B), which serves as an internal control for gel loading. FIG. 8C is a bar graph of the relative expression of D2-2 after correction for gel loading based on β actin expression. See Section 6.1.5 for experimental details.

Figure 9:
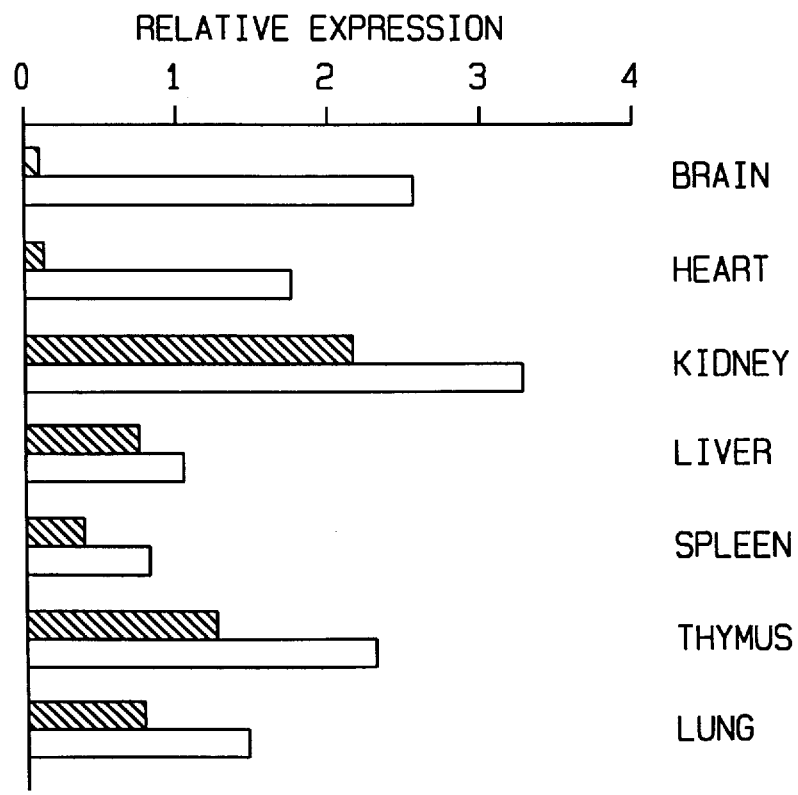

FIG. 9 illustrates expression of clone D2-2 in fetal compared to adult tissue. See text Section 6.1.6 for experimental details.

5. DETAILED DESCRIPTION OF THE INVENTION

The present invention relates to nucleotide sequences of D2-2 genes, and amino acid sequences of their encoded proteins. The invention further relates to fragments and other derivatives, and analogs, of D2-2 proteins.

Nucleic acids encoding such fragments or derivatives are also within the scope of the invention. The invention provides D2-2 genes and their encoded proteins of humans and related genes (homologs) in other species. In specific embodiments, the D2-2 genes and proteins are from vertebrates, or more particularly, mammals. In a preferred embodiment of the invention, the D2-2 genes and proteins are of human origin. Production of the foregoing nucleic acids, proteins and derivatives, e.g., by recombinant methods, is provided.

D2-2 is a gene provided by the present invention, identified by the method of the invention, and that is expressed at high levels in glioblastoma multiforme tissue as well as certain others forms of tumors and cancers.

The invention also relates to D2-2 derivatives and analogs of the invention which are functionally active, i.e., they are capable of displaying one or more functional activities described herein associated with a full-length (wild-type) D2-2 protein. Such functional activities include but are not limited to antigenicity, i.e., ability to bind (or compete with D2-2 for binding) to an anti-D2-2 antibody, immunogenicity, i.e., ability to generate antibody which binds to D2-2, and ability to bind (or compete with D2-2 for binding) to a receptor/ligand for D2-2.

The invention further relates to fragments (and derivatives and analogs thereof) of D2-2 which comprise one or more domains of the D2-2 protein.

Antibodies to D2-2, its derivatives and analogs, are additionally provided.

The present invention also relates to therapeutic and diagnostic methods and compositions based on D2-2 proteins and nucleic acids and anti-D2-2 antibodies. The invention provides for treatment of disorders of overproliferation (e.g., cancer and hyperproliferative disorders) by administering compounds that decrease D2-2 activity (e.g., antibodies, D2-2 antisense nucleic acids).

The invention also provides methods of treatment of disorders involving deficient cell proliferation or in which cell proliferation (growth) is otherwise desirable (e.g., growth deficiencies, degenerative disorders, lesions, physical trauma) by administering compounds that promote D2-2 function.

Promotion of D2-2 function can also be done to grow larger farm animals and plants.

Animal models, diagnostic methods and screening methods for predisposition to disorders are also provided by the invention.

The invention is illustrated by way of examples infra which disclose, inter alia, the isolation and characterization of D2-2, and patterns of expression of D2-2 in certain tumors and during development (see Section 6).

For clarity of disclosure, and not by way of limitation, the detailed description of the invention is divided into the subsections which follow.

5.1. ISOLATION OF THE D2-2 GENE

The invention relates to the nucleotide sequences of D2-2 nucleic acids. In specific embodiments, D2-2 nucleic acids comprise the cDNA sequences of SEQ ID NO: 1, or the coding regions thereof, or nucleotide sequences acids encoding a D2-2 protein (e.g., a protein having the sequence of SEQ ID NO: 7). The invention provides purified nucleic acids consisting of at least 6 contiguous nucleotides (i.e., a hybridizable portion) of a D2-2 sequence; in other embodiments, the nucleic acids consist of contiguous nucleotides of at least 8 nucleotides, 25 nucleotides, 50 nucleotides, 100 nucleotides, 150 nucleotides, 200 nucleotides, or 250 nucleotides of a D2-2 sequence. In another embodiment, the nucleic acids are smaller than 35, 200 or 250 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, 200, or 250 nucleotides of a D2-2 gene. In a specific embodiment, a nucleic acid which is hybridizable to a D2-2 nucleic acid (e.g., having sequence SEQ ID NO: 2), or to a nucleic acid encoding a D2-2 derivative, under conditions of low stringency is provided.

By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2× SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65°–68° C. and reexposed to film. Other conditions of low stringency which may be used are well known in the art (e.g., as employed for cross-species hybridizations).

In another specific embodiment, a nucleic acid which is hybridizable to a D2-2 nucleic acid under conditions of high stringency is provided. By way of example and not limitation, procedures using such conditions of high stringency are as follows: Prehybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2× SSC, 0.01% PVP, 0.01% Ficoll, and 0.01 BSA. This is followed by a wash in 0.1× SSC at 50° C. for 45 min before autoradiography. Other conditions of high stringency which may be used are well known in the art.

In another specific embodiment, a nucleic acid which is hybridizable to a D2-2 nucleic acid under conditions of moderate stringency is provided.

Various other stringency conditions which promote nucleic acid hybridization can be used. For example, hybridization in 6× SSC at about 45° C., followed by washing in 2× SSC at 50° C. may be used. Alternatively, the salt concentration in the wash step can range from low stringency of about 5× SSC at 50° C., to moderate stringency of about 2× SSC at 50° C., to high stringency of about 0.2× SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M NaHPO$_4$ (pH7.2)/1 mM EDTA/7% SDS, or hybridization in 50% formamide/0.25M NaHPO$_4$ (pH 7.2)/0.25M NaCl/1 mM EDTA/7% SDS; followed by washing in 40 mM NaHPO$_4$ (pH 7.2)/1 mM EDTA/5% SDS at 42° C. or in 40 mM NaHPO$_4$ (pH7.2) 1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y.

Nucleic acids encoding derivatives and analogs of D2-2 proteins (see Sections 5.6 and 5.6.1), and D2-2 antisense nucleic acids (see Section 5.9.2.1.1) are additionally provided. As is readily apparent, as used herein, a "nucleic acid encoding a fragment or portion of a D2-2 protein" shall be construed as referring to a nucleic acid encoding only the recited fragment or portion of the D2-2 protein and not the other contiguous portions of the D2-2 protein as a continuous sequence.

Fragments of D2-2 nucleic acids comprising regions conserved between other D2-2 nucleic acids, of the same or different species, are also provided. Nucleic acids encoding one or more D2-2 domains are provided.

Specific embodiments for the cloning of a D2-2 gene, presented as a particular example but not by way of limitation, follow:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed D2-2 product. In one embodiment, anti-D2-2 antibodies can be used for selection.

In another embodiment, polymerase chain reaction (PCR) is used to amplify the desired sequence in a genomic or cDNA library, prior to selection. Oligonucleotide primers representing known D2-2 sequences can be used as primers in PCR. In a preferred aspect, the oligonucleotide primers represent at least part of the D2-2 sequence presented in FIG. 3 (SEQ ID NO: 1). The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp). The DNA being amplified can include mRNA, cDNA, or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known D2-2 nucleotide sequence and the nucleic acid homolog being isolated. For cross species hybridization, low stringency conditions are preferred. For same species hybridization, moderately stringent conditions are preferred. After successful amplification of a segment of a D2-2 homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding D2-2 proteins and D2-2 analogs may be identified.

The above-methods are not meant to limit the following general description of methods by which clones of D2-2 may be obtained.

Any eukaryotic cell potentially can serve as the nucleic acid source for the molecular cloning of the D2-2 gene. The nucleic acid sequences encoding D2-2 can be isolated from vertebrate sources, including mammalian sources, such as porcine, bovine, feline, and equine, canine, human, as well as additional primate sources, avian, reptilian, amphibian, piscine, etc. sources, non-vertebrate sources such as insects, from plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a D2-2 (of any species) gene or its specific RNA, or a fragment thereof (see Section 5.6), is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the asis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, promotion of cell proliferation activity, substrate binding activity, or antigenic properties of D2-2. If an antibody to D2-2 is available, the D2-2 protein may be identified by binding of labeled antibody to the putatively D2-2 synthesizing clones, in an ELISA (enzyme-linked immunosorbent assay)-type procedure.

The D2-2 gene can also be identified by mRNA selection by nucleic acid hybridization followed by in vitro translation. In this procedure, fragments are used to isolate complementary mRNAs by hybridization. Such DNA fragments may represent available, purified D2-2 DNA of another species (e.g., human, mouse, etc.). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against D2-2 protein. A radiolabelled D2-2 cDNA can be synthesized using the selected mRNA (from the adsorbed polysomes) as a template. The radiolabelled mRNA or cDNA may then be used as a probe to identify the D2-2 DNA fragments from among other genomic DNA fragments.

Alternatives to isolating the D2-2 genomic DNA include, but are not limited to, chemically synthesizing the gene sequence itself from a known sequence or making cDNA to the mRNA which encodes the D2-2 protein. For example, RNA for cDNA cloning of the D2-2 gene can be isolated from cells which express D2-2. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and D2-2 gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated D2-2 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The D2-2 sequences provided by the present invention include those nucleotide sequences encoding substantially the same amino acid sequences as found in native D2-2 proteins, and those encoded amino acid sequences with functionally equivalent amino acids, as well as those encoding other D2-2 derivatives or analogs, as described in Sections 5.6 and 5.6.1 infra for D2-2 derivatives and analogs.

5.2. EXPRESSION OF THE D2-2 GENE

The nucleotide sequence coding for a D2-2 protein or a functionally active analog or fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native D2-2 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, the human D2-2 gene is expressed, or a sequence encoding a functionally active portion of human D2-2. In yet another embodiment, a fragment of D2-2 comprising a domain of the D2-2 protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a D2-2 protein or peptide fragment may be regulated by a second nucleic acid sequence so that the D2-2 protein or peptide is expressed in a host transformed with the recombinant DNA molecule. For example, expression of a D2-2 protein may be controlled by any promoter/enhancer element known in the art. Promoters which may be used to control D2-2 expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21-25); see also "Useful proteins from recombinant bacteria" in Scientific American, 1980, 242:74–94; plant expression vectors comprising the nopaline synthetase promoter region (Herrera-Estrella et al., 1983, Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338-340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to a D2-2-encoding nucleic acid, one or more origins of replication, and, optionally, one or more selectable markers (e.g., an antibiotic resistance gene).

In a specific embodiment, an expression construct is made by subcloning a D2-2 coding sequence into the EcoRI restriction site of each of the three pGEX vectors (Glutathione S-Transferase expression vectors; Smith and Johnson, 1988, Gene 7:31–40). This allows for the expression of the D2-2 protein product from the subclone in the correct reading frame.

Expression vectors containing D2-2 gene inserts can be identified by three general approaches: (a) nucleic acid hybridization, (b) presence or absence of "marker" gene functions, and (c) expression of inserted sequences. In the first approach, the presence of a D2-2 gene inserted in an expression vector can be detected by nucleic acid hybridization using probes comprising sequences that are homologous to an inserted D2-2 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a D2-2 gene in the vector. For example, if the D2-2 gene is inserted within the marker gene sequence of the vector, recombinants containing the D2-2 insert can be identified by the absence of the marker gene function. In the third approach, recombinant expression vectors can be identified by assaying the D2-2 product expressed by the recombinant. Such assays can be based, for example, on the physical or functional properties of the D2-2 protein in in vitro assay systems, e.g., binding with anti-D2-2 antibody, promotion of cell proliferation.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered D2-2 protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the D2-2 protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3. IDENTIFICATION AND PURIFICATION OF THE D2-2 GENE PRODUCTS

In particular aspects, the invention provides amino acid sequences of D2-2, preferably human D2-2, and fragments and derivatives thereof which comprise an antigenic determinant (i.e., can be recognized by an antibody) or which are otherwise functionally active, as well as nucleic acid sequences encoding the foregoing. "Functionally active" D2-2 material as used herein refers to that material displaying one or more functional activities associated with a full-length (wild-type) D2-2 protein, e.g., promotion of cell proliferation, binding to a D2-2 substrate or D2-2 binding partner, antigenicity (binding to an anti-D2-2 antibody), immunogenicity, etc.

In a specific embodiment, the invention provides proteins comprising, having, or consisting essentially of a sequence of amino acids having a sequence at least 70%, preferably 80% identical with SEQ ID NO: 7. In other specific embodiments, the invention provides fragments of a D2-2 protein consisting of at least 6 amino acids, 10 amino acids, 50 amino acids, or of at least 75 amino acids. In other embodiments, the invention provides proteins comprising, having, or consisting essentially of a sequence of amino acids 100% identical with SEQ ID NO: 15, SEQ ID NO: 17, or SEQ ID NO: 19, or any combination of the foregoing, of a D2-2 protein. Fragments or proteins comprising such sequences are particularly advantageously used for immunotherapy as described below e.g., in Section 5.11. Fragments, or proteins comprising fragments, lacking some or all of the foregoing regions of a D2-2 protein are also provided. Nucleic acids encoding the foregoing are provided.

Once a recombinant which expresses the D2-2 gene sequence is identified, the gene product can be analyzed. This is achieved by assays based on the physical or functional properties of the product, including radioactive labelling of the product followed by analysis by gel electrophoresis, immunoassay, etc.

Once the D2-2 protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once a D2-2 protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In another alternate embodiment, native D2-2 proteins can be purified from natural sources, by standard methods such as those described above (e.g., immunoaffinity purification).

In a specific embodiment of the present invention, such D2-2 proteins, whether produced by recombinant DNA techniques or by chemical synthetic methods or by purification of native proteins, include but are not limited to those containing, as a primary amino acid sequence, all or part of the amino acid sequence substantially as depicted in FIG. 3 (SEQ ID NO: 7), as well as fragments and other derivatives, and analogs thereof, including proteins homologous thereto.

5.4. STRUCTURE OF THE D2-2 GENE AND PROTEIN

The structure of the D2-2 gene and protein can be analyzed by various methods known in the art.

5.4.1. GENETIC ANALYSIS

The cloned DNA or cDNA corresponding to the D2-2 gene can be analyzed by methods including but not limited to Southern hybridization (Southern, E. M., 1975, J. Mol. Biol. 98:503–517), Northern hybridization (see e.g., Freeman et al., 1983, Proc. Natl. Acad. Sci. U.S.A. 80:4094–4098), restriction endonuclease mapping (Sambrook et al., 1989, Molecular Cloning, A Laboratory Manual, 2d Ed., Cold Spring Harbor Laboratory Press, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a D2-2-specific probe can allow the detection of the D2-2 gene in DNA from various cell types. Methods of amplification other than PCR are commonly known and can also be employed.

In one embodiment, Southern hybridization can be used to determine the genetic linkage of D2-2. Northern hybridization analysis can be used to determine the expression of the D2-2 gene. Various cell types, at various states of development or activity can be tested for D2-2 expression. The stringency of the hybridization conditions for both Southern and Northern hybridization can be manipulated to ensure detection of nucleic acids with the desired degree of relatedness to the specific D2-2 probe used. Modifications of these methods and other methods commonly known in the art can be used.

Restriction endonuclease mapping can be used to roughly determine the genetic structure of the D2-2 gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. PROTEIN ANALYSIS

The amino acid sequence of the D2-2 protein can be derived by deduction from the DNA sequence, or alternatively, by direct sequencing of the protein, e.g., with an automated amino acid sequencer.

The D2-2 protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the D2-2 protein and the corresponding regions of the gene sequence which encode such regions.

Secondary, structural analysis (Chou, P. and Fasman, G., 1974, Biochemistry 13:222) can also be done, to identify regions of D2-2 that assume specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. ANTIBODIES AND IMMUNE CELLS TO D2-2

5.5.1. GENERATION OF ANTIBODIES TO D2-2 PROTEINS AND DERIVATIVES THEREOF

According to the invention, D2-2 protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a human D2-2 protein are produced. In another embodiment, antibodies to a domain of a D2-2 protein are produced. In a specific embodiment, fragments of a D2-2 protein identified as hydrophilic are used as immunogens for antibody production.

In another specific embodiment, the antibody to a human D2-2 protein is a bispecific antibody (see generally, e.g. Fanger and Drakeman, 1995, Drug News and Perspectives 8: 133–137). Such a bispecific antibody is genetically engineered to recognize both (1) a human D2-2 epitope and (2) one of a variety of "trigger" molecules, e.g. Fc receptors on myeloid cells, and CD3 and CD2 on T cells, that have been identified as being able to cause a cytotoxic T-cell to destroy a particular target. Such bispecific antibodies can be prepared either by chemical conjugation, hybridoma, or recombinant molecular biology techniques known to the skilled artisan.

Various procedures known in the art may be used for the production of polyclonal antibodies to a D2-2 protein or derivative or analog. In a particular embodiment, rabbit polyclonal antibodies to an epitope of a D2-2 protein encoded by a sequence of SEQ ID NO: 1, or a subsequence thereof (e.g., SEQ ID NO: 6), can be obtained. For the production of antibody, various host animals can be immunized by injection with the native D2-2 protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a D2-2 protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing technology described in PCT/US90/02545. According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, PROC. NATL. ACAD. SCI. U.S.A. 81:6851–6855; Neuberger et al., 1984, Nature 312:604–608; Takeda et al., 1985, Nature 314:452–454) by splicing the genes from a mouse antibody molecule specific for D2-2 together with genes from a human antibody molecule of appropriate biological activity can be used; such antibodies are within the scope of this invention.

According to the invention, techniques described for the production of single chain antibodies (U.S. Pat. No. 4,946,778) can be adapted to produce D2-2-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for D2-2 proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a D2-2 protein, one may assay generated hybridomas for a product which binds to a D2-2 fragment containing such domain. For selection of an antibody that specifically binds a first D2-2 homolog but which does not specifically bind a different D2-2 homolog, one can select on the basis of positive binding to the first D2-2 homolog and a lack of binding to the second D2-2 homolog.

Antibodies specific to a domain of a D2-2 protein are also provided.

The foregoing antibodies can be used in methods known in the art relating to the localization and activity of the D2-2 protein sequences of the invention, e.g., for imaging these proteins, measuring levels thereof in appropriate physiological samples, in diagnostic methods, etc.

In another embodiment of the invention (see infra), anti-D2-2 antibodies and fragments thereof containing the binding domain are Therapeutics.

5.5.2. GENERATION OF ACTIVATED IMMUNE CELLS BY EXPOSURE TO D2-2 PROTEINS OR DERIVATIVES THEREOF

According to the invention D2-2 protein, its fragments or other derivatives, or analogs thereof, may be used to generate activated immune cells that immunospecifically bind a portion of D2-2 and are useful to produce an immunotherapeutic growth inhibiting response against a primary or metastatic tumor expressing D2-2. Such activated immune cells include but are not limited to dendritic cells and cytotoxic T-cells. In particular, a D2-2 protein or peptide provided by the invention, that has an HLA-A2$^+$ motif, e.g., SEQ ID NO: 15, SEQ ID NO: 17, SEQ ID NO: 19, can be used to generate activated immune cells. Dendritic cells are known to be the primary type of antigen-presenting cell and addition of such a protein or peptide to dendritic cells by exposing them to the protein or peptide enables the dendritic cell to activate cytotoxic T-cells specific for the peptide (See generally, Tjoa et al., 1996, Prostate 28:65–59). Such activated dendritic cells (HLA matched to the recipient) can be used as a Therapeutic (see Section 5.11) that targets and kills tumor cells. In addition, a protein or peptide provided by the invention, that has an HLA-A2+ motif can be used to activate cytotoxic T-cells (HLA matched to the recipient) in vitro. Such activated T-cells can be used as a Therapeutic (see Section 5.11) that targets and kills tumor cells.

5.6. D2-2 PROTEINS, DERIVATIVES AND ANALOGS

The invention further relates to D2-2 proteins, and derivatives (including but not limited to fragments) and analogs of D2-2 proteins. Nucleic acids encoding D2-2 protein derivatives and protein analogs are also provided. In one embodiment, the D2-2 proteins are encoded by the D2-2 nucleic acids described in Section 5.1 supra. In particular aspects, the proteins, derivatives, or analogs are of D2-2 proteins of animals, e.g., fly, frog, mouse, rat, pig, cow, dog, monkey, human, or of plants.

The production and use of derivatives and analogs related to D2-2 are within the scope of the present invention. In a specific embodiment, the derivative or analog is functionally active, i.e., capable of exhibiting one or more functional activities associated with a full-length, wild-type D2-2 protein. As one example, such derivatives or analogs which have the desired immunogenicity or antigenicity can be used, for example, in immunoassays, for immunization, for inhibition of D2-2 activity, etc. Derivatives or analogs that retain, or alternatively lack or inhibit, a desired D2-2 property of interest (e.g., binding to D2-2 binding partner, promotion of cell proliferation), can be used as inducers, or inhibitors, respectively, of such property and its physiological correlates. A specific embodiment relates to a D2-2 fragment that can be bound by an anti-D2-2 antibody. Derivatives or analogs of D2-2 can be tested for the desired activity by procedures known in the art, including but not limited to the assays described in Sections 5.7 and 5.9.

In particular, D2-2 derivatives can be made by altering D2-2 sequences by substitutions, additions or deletions that provide for functionally equivalent molecules. Due to the degeneracy of nucleotide coding sequences, other DNA sequences which encode substantially the same amino acid sequence as a D2-2 gene may be used in the practice of the present invention. These include but are not limited to nucleotide sequences comprising all or portions of D2-2 genes which are altered by the substitution of different codons that encode a functionally equivalent amino acid residue within the sequence, thus producing a silent change. Likewise, the D2-2 derivatives of the invention include, but are not limited to, those containing, as a primary amino acid sequence, all or part of the amino acid sequence of a D2-2 protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic)

amino acids include arginine, lysine and histidine. The negatively charged (acidic) amino acids include aspartic acid and glutamic acid.

In a specific embodiment of the invention, proteins consisting of or comprising a fragment of a D2-2 protein consisting of at least 10 (continuous) amino acids of the D2-2 protein is provided. In other embodiments, the fragment consists of at least 20 or 50 amino acids of the D2-2 protein. In specific embodiments, such fragments are not larger than 35, 100 or 200 amino acids. Derivatives or analogs of D2-2 include but are not limited to those molecules comprising regions that are substantially homologous to D2-2 or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding D2-2 sequence, under stringent, moderately stringent, or nonstringent conditions.

The D2-2 derivatives and analogs of the invention can be produced by various methods known in the art. The manipulations which result in their production can occur at the gene or protein level. For example, the cloned D2-2 gene sequence can be modified by any of numerous strategies known in the art (Sambrook et al., 1989, Molecular Cloning, A Laboratory Manual, 2d Ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of D2-2, care should be taken to ensure that the modified gene remains within the same translational reading frame as D2-2, uninterrupted by translational stop signals, in the gene region where the desired D2-2 activity is encoded.

Additionally, the D2-2-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the D2-2 sequence may also be made at the protein level. Included within the scope of the invention are D2-2 protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of D2-2 can be chemically synthesized. For example, a peptide corresponding to a portion of a D2-2 protein which comprises the desired domain (see Section 5.6.1), or which mediates the desired activity in vitro, can be synthesized by use of a peptide synthesizer. Furthermore, if desired, nonclassical amino acids or chemical amino acid analogs can be introduced as a substitution or addition into the D2-2 sequence. Nonclassical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the D2-2 derivative is a chimeric, or fusion, protein comprising a D2-2 protein or fragment thereof (preferably consisting of at least a domain or motif of the D2-2 protein, or at least 10 amino acids of the D2-2 protein) joined at its amino- or carboxy-terminus via a peptide bond to an amino acid sequence of a different protein. In one embodiment, such a chimeric protein is produced by recombinant expression of a nucleic acid encoding the protein (comprising a D2-2-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of D2-2 fused to any heterologous protein-encoding sequences may be constructed. A specific embodiment relates to a chimeric protein comprising a fragment of D2-2 of at least six amino acids.

In another specific embodiment, the D2-2 derivative is a molecule comprising a region of homology with a D2-2 protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to a D2-2 domain (see Section 5.6.1) or a portion thereof.

Other specific embodiments of derivatives and analogs are described in the subsections below and examples sections infra.

5.6.1. DERIVATIVES OF D2-2 CONTAINING ONE OR MORE DOMAINS OF THE PROTEIN

In a specific embodiment, the invention relates to D2-2 derivatives and analogs, in particular D2-2 fragments and derivatives of such fragments, that comprise, or alternatively consist of, one or more domains of a D2-2 protein, including but not limited to SEQ ID NO: 7, amino acid sequences of D2-2 that contain an HLA-A2$^+$ motif e.g. SEQ ID NO: 15, SEQ ID NO: 17, SEQ ID NO: 19, functional (e.g., binding) fragments of any of the foregoing, or any combination of the foregoing. In particular examples relating to human D2-2 proteins, such domains are identified in FIG. 3.

A specific embodiment relates to molecules comprising specific fragments of D2-2 that are those fragments in the respective D2-2 protein most homologous to specific fragments of a human or other primate D2-2 protein. A fragment comprising a domain of a D2-2 homolog can be identified by protein analysis methods as described in Sections 5.3.2 or 6.

In another specific embodiment, a molecule is provided that comprises one or more domains (or functional portion thereof) of a D2-2 protein but that also lacks one or more domains (or functional portion thereof) of a D2-2 protein. In another embodiment, a molecule is provided that comprises one or more domains (or functional portion thereof) of a D2-2 protein, and that has one or more mutant (e.g., due to deletion or point mutation(s)) domains of a D2-2 protein (e.g., such that the mutant domain has decreased function).

5.7. ASSAYS OF D2-2 PROTEINS, DERIVATIVES AND ANALOGS

The functional activity of D2-2 proteins, derivatives and analogs can be assayed by various methods.

For example, in one embodiment, where one is assaying for the ability to bind or compete with wild-type D2-2 for binding to anti-D2-2 antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a D2-2-binding protein is identified, the binding can be assayed, e.g., by means well-known in the art. In another embodiment, physiological correlates of D2-2 binding t o its substrates (signal transduction) can be assayed.

In addition, assays that can be used to detect or measure the ability to inhibit, or alternatively promote, cell proliferation are described in Section 5.9.

Other methods will be known to the skilled artisan and are within the scope of the invention.

5.8. DIAGNOSIS AND SCREENING

D2-2 proteins, analogs, derivatives, and subsequences thereof, D2-2 nucleic acids (and sequences complementary thereto), anti-D2-2 antibodies, have uses in diagnostics. Such molecules can be used in assays, such as immunoassays, to detect, prognose, diagnose, or monitor various conditions, diseases, and disorders affecting D2-2 expression, or monitor the treatment thereof. In particular, such an immunoassay is carried out by a method comprising contacting a sample derived from a patient with an anti-D2-2 antibody under conditions such that immunospecific binding can occur, and detecting or measuring the amount of any immunospecific binding by the antibody. In a specific aspect, such binding of antibody, in tissue sections, can be used to detect aberrant D2-2 localization or aberrant (e.g., high, low or absent) levels of D2-2. In a specific embodiment, antibody to D2-2 can be used to assay in a patient tissue or serum sample for the presence of D2-2 where an aberrant level of D2-2 is an indication of a diseased condition. By "aberrant levels," i s meant increased or decreased levels relative to that present, or a standard level representing that present, in an analogous sample from a portion of the body or from a subject not having the disorder. In a specific embodiment, antibody to D2-2 can be used to assay and screen tissues or bodily fluids including but not limited to spinal fluid and brain tissue for elevated levels of D2-2 expression indicative of a tumor.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

D2-2 genes and related nucleic acid sequences and subsequences, including complementary sequences, can also be used in hybridization assays. D2-2 nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in D2-2 expression and/or activity as described supra. In particular, such a hybridization assay is carried out by a method comprising contacting a sample containing nucleic acid with a nucleic acid probe capable of hybridizing to D2-2 DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, by detecting increased levels of D2-2 protein, D2-2 RNA, or D2-2 functional activity or by detecting mutations in D2-2 RNA, DNA or protein (e.g., translocations in D2-2 nucleic acids, truncations in the D2-2 gene or protein, changes in nucleotide or amino acid sequence relative to wild-type D2-2) that cause increased expression or activity of D2-2. Such diseases and disorders include but are not limited to those tumors or tissue types mentioned in Section 6 in which D2-2 is overexpressed. By way of example, levels of D2-2 protein can be detected by immunoassay, levels of D2-2 RNA can be detected by hybridization assays (e.g., Northern blots, dot blots), translocations and point mutations in D2-2 nucleic acids can be detected by Southern blotting, RFLP analysis, PCR using primers that preferably generate a fragment spanning at least most of the D2-2 gene, sequencing of the D2-2 genomic DNA or cDNA obtained from the patient, etc.

In a preferred embodiment, levels of D2-2 mRNA or protein in a patient sample are detected or measured, in which increased levels indicate that the subject has, or has a predisposition to developing, a malignancy or hyperproliferative disorder; in which the increased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting decreased levels of D2-2 protein, D2-2 RNA, or D2-2 functional activity, or by detecting mutations in D2-2 RNA, DNA or protein (e.g., translocations in D2-2 nucleic acids, truncations in the gene or protein, changes in nucleotide or amino acid sequence relative to wild-type D2-2) that cause decreased expression or activity of D2-2. Such diseases and disorders include but are not limited to those tumors and tissue types mentioned in Section 6 and its subsections in which D2-2 is overexpressed. By way of example, levels of D2-2 protein, levels of D2-2 RNA, D2-2 binding activity, and the presence of translocations or point mutations can be determined as described above.

In a specific embodiment, levels of D2-2 mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

Kits for diagnostic use are also provided, that comprise in one or more containers an anti-D2-2 antibody, and, optionally, a labeled binding partner to the antibody. Alternatively, the anti-D2-2 antibody can be labeled (with a detectable marker, e.g., a chemiluminescent, enzymatic, fluorescent, or radioactive moiety). A kit is also provided that comprises in one or more containers a nucleic acid probe capable of hybridizing to D2-2 RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a D2-2 nucleic acid. A kit can optionally further comprise in a container a predetermined amount of a purified D2-2 protein or nucleic acid, e.g., for use as a standard or control.

5.9. THERAPEUTIC USES

The invention provides for treatment or prevention of various diseases and disorders by administration of a therapeutic compound (termed herein "Therapeutic"). Such "Therapeutics" include but are not limited to: D2-2 proteins and analogs and derivatives (including fragments) thereof (e.g., as described hereinabove); antibodies thereto (as described hereinabove); nucleic acids encoding the D2-2 proteins, analogs, or derivatives (e.g., as described hereinabove); D2-2 antisense nucleic acids, and D2-2 agonists and antagonists. Disorders involving tumorigenesis or cell overproliferation are treated or prevented by administration of a Therapeutic that antagonizes D2-2 function. Disorders in which cell proliferation is deficient or is desired are treated or prevented by administration of a Therapeutic that promotes D2-2 function. See details in the subsections below.

Generally, it is preferred to administer a product of a species origin or species reactivity (in the case of antibodies) that is the same as that of the recipient. Thus, in a preferred embodiment, a human D2-2 protein, derivative, or analog, or nucleic acid, or an antibody to a human D2-2 protein, is therapeutically or prophylactically administered to a human patient.

Additional descriptions and sources of Therapeutics that can be used according to the invention are found in Sections 5.1 through 5.7 herein.

5.9.1. TREATMENT AND PREVENTION OF DISORDERS INVOLVING OVERPROLIFERATION OF CELLS

Diseases and disorders involving cell overproliferation are treated or prevented by administration of a Therapeutic that antagonizes (i.e., inhibits) D2-2 function. Examples of such a Therapeutic include but are not limited to D2-2 antibodies, D2-2 antisense nucleic acids, derivatives, or analogs that are functionally active, particularly that are active in inhibiting cell proliferation (e.g., as demonstrated in in vitro assays or in animal models or in Drosophila). Other Therapeutics that can be used, e.g., D2-2 antagonists, can be identified using in vitro assays or animal models, examples of which are described infra.

In specific embodiments, Therapeutics that inhibit D2-2 function are administered therapeutically (including prophylactically): (1) in diseases or disorders involving an increased (relative to normal or desired) level of D2-2 protein or function, for example, in patients where D2-2 protein is overexpressed, genetically defective, or biologically hyperactive; or (2) in diseases or disorders wherein in vitro (or in vivo) assays (see infra) indicate the utility of D2-2 antagonist administration. The increased level in D2-2 protein or function can be readily detected, e.g., by obtaining a patient tissue sample (e.g., from biopsy tissue) and assaying it in vitro for RNA or protein levels, structure and/or activity of the expressed D2-2 RNA or protein. Many methods standard in the art can be thus employed, including but not limited to immunoassays to detect and/or visualize D2-2 protein (e.g., Western blot, immunoprecipitation followed by sodium dodecyl sulfate polyacrylamide gel electrophoresis, immunocytochemistry, etc.) and/or hybridization assays to detect D2-2 expression by detecting and/or visualizing D2-2 mRNA (e.g., Northern assays, dot blots, in situ hybridization, etc.), etc.

Diseases and disorders involving cell overproliferation that can be treated or prevented include but are not limited to malignancies, premalignant conditions (e.g., hyperplasia, metaplasia, dysplasia), benign tumors, hyperproliferative disorders, benign dysproliferative disorders, etc. Examples of these are detailed below.

5.9.1.1. MALIGNANCIES

Malignancies and related disorders that can be treated or prevented by administration of a Therapeutic that inhibits D2-2 function include but are not limited to those listed in Table 1 (for a review of such disorders, see Fishman et al., 1985, Medicine, 2d Ed., J. B. Lippincott Co., Philadelphia).

TABLE 1

MALIGNANCIES AND RELATED DISORDERS

Leukemia
  acute leukemia
    acute lymphocytic leukemia
    acute lymphoblastic leukemia
    acute myelocytic leukemia
      myeloblastic
      myelogenous
      promyelocytic
      myelomonocytic
      monocytic

TABLE 1-continued

MALIGNANCIES AND RELATED DISORDERS erythroleukemia
  chronic leukemia
    chronic myelocytic (granulocytic) leukemia
    chronic myelogenous leukemia
    chronic lymphocytic leukemia
Polycythemia vera
Lymphoma
  Hodgkin's disease
  non-Hodgkin's disease
Multiple myeloma
Waldenström's macroglobulinemia
Heavy chain disease
Solid tumors
  sarcomas and carcinomas
    adenocarcinoma
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    colorectal adenocarcinoma
    colon tumor metastatic to brain
    lung carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    uterine cancer
    testicular tumor
    lung carcinoma
    small cell lung carcinoma
    bladder carcinoma
    epithelial carcinoma
    glioblastoma
    glioma
    astrocytoma
    medulloblastoma
    craniopharyngioma
    ependymoma
    pinealoma
    hemangioblastoma
    acoustic neuroma
    oligodendroglioma
    meningioma
    melanoma
    neuroblastoma
    retinoblastoma In specific embodiments, malignancy or dysproliferative changes (such as metaplasias and dysplasias), or hyperproliferative disorders, are treated or prevented in the brain, breast, colon, prostate, lung, or skin. In other specific embodiments, carcinoma, melanoma, or leukemia is treated or prevented.

5.9.1.2. PREMALIGNANT CONDITIONS

The Therapeutics of the invention that antagonize D2-2 activity can also be administered to treat premalignant conditions and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic that inhibits D2-2 function. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are preneoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.)

In another specific embodiment, a Therapeutic of the invention is administered to a human patient to prevent progression to brain, breast, colon, prostate, lung, or skin. In other specific embodiments, carcinoma, melanoma, or leukemia is treated or prevented.

5.9.1.3. GENE THERAPY

In a specific embodiment, anti-sense nucleic acids complementary to a sequence encoding a D2-2 protein or functional derivative thereof, are administered to inhibit D2-2 function, by way of gene therapy. Gene therapy refers to therapy performed by the administration of a nucleic acid to a subject. In this embodiment of the invention, the antisense nucleic acid mediates a therapeutic effect by inhibiting D2-2 transcription and translation.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one embodiment, the Therapeutic comprises an D2-2 sense or antisense nucleic acid that is part of an expression vector that expresses a D2-2 protein or fragment or chimeric protein thereof in a suitable host. In particular, such a nucleic acid has a promoter operably linked to the D2-2 coding region, said promoter being inducible or constitutive, and, optionally, tissue-specific. In another particular embodiment, a nucleic acid molecule is used in which the D2-2 coding sequences and any other desired sequences are flanked by regions that promote homologous recombination at a desired site in the genome, thus providing for intrachromosomal expression of the D2-2 nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the D2-2 nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The D2-2 nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234.

Adeno-associated virus (AAV) has also been proposed for use in gene therapy (Walsh et al., 1993, Proc. Soc. Exp. Biol. Med. 204:289–300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a D2-2 nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, 1992, Cell 71:973–985).

Epithelial stem cells (ESCs) or keratinocytes can be obtained from tissues such as the skin and the lining of the gut by known procedures (Rheinwald, 1980, Meth. Cell Bio. 21A:229) . In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a D2-2 protein or functional derivative thereof are described in Section 5.8.2.2.2.

5.9.2. TREATMENT AND PREVENTION OF HYPERPROLIFERATIVE AND DYSPROLIFERATIVE DISORDERS

Diseases and disorders involving an increase in cell proliferation (growth) or in which cell proliferation is otherwise undesirable, are treated or prevented by administration of a Therapeutic that antagonizes (inhibits) D2-2 function. Therapeutics that can be used include but are not limited to anti-D2-2 antibodies (and fragments and derivatives thereof containing the binding region thereof), D2-2 antisense nucleic acids, and D2-2 nucleic acids that are dysfunctional (e.g., due to a heterologous (non-D2-2 sequence) insertion within the D2-2 coding sequence) that are used to "knockout" endogenous D2-2 function by homologous recombination (see, e.g., Capecchi, 1989, Science 244:1288–1292). In a specific embodiment of the invention, a nucleic acid containing a portion of a D2-2 gene in which D2-2 sequences flank (are both 5' and 3' to) a different gene sequence, is used, as a D2-2 antagonist, to promote D2-2 inactivation by homologous recombination (see also Koller and Smithies, 1989, Proc. Natl. Acad. Sci. USA 86:8932–8935; Zijlstra et al., 1989, Nature 342:435–438). Other Therapeutics that inhibit D2-2 function can be identified by use of known convenient in vitro assays, e.g., based on their ability to inhibit binding of D2-2 to another protein or inhibit any known D2-2 function, as preferably assayed in vitro or in cell culture, although genetic assays in Drosophila or another species may also be employed. Preferably, suitable in vitro or in vivo assays, are utilized to determine the effect of a specific Therapeutic and whether its administration is indicated for treatment of the affected tissue.

In specific embodiments, Therapeutics that inhibit D2-2 function are administered therapeutically (including prophylactically): (1) in diseases or disorders involving an increased (relative to normal or desired) level of D2-2 protein or function, for example, in patients where D2-2 protein is overactive or overexpressed; or (2) in diseases or disorders wherein in vitro (or in vivo) assays (see infra) indicate the utility of D2-2 antagonist administration. The increased levels in D2-2 protein or function can be readily detected, e.g., by quantifying protein and/or RNA, by obtaining a patient tissue sample (e.g., from biopsy tissue) and assaying it in vitro for RNA or protein levels, structure and/or activity of the expressed D2-2 RNA or protein. Many methods standard in the art can be thus employed, including but not limited to immunoassays to detect and/or visualize D2-2 protein (e.g., Western blot, immunoprecipitation followed by sodium dodecyl sulfate polyacrylamide gel electrophoresis, immunocytochemistry, etc.) and/or hybridization assays to detect D2-2 expression by detecting and/or visualizing respectively D2-2 mRNA (e.g., Northern assays, dot blots, in situ hybridization, etc.), etc.

In other embodiments, chemical mutagenesis, or homologous recombination with an insertionally inactivated D2-2 gene (see Capecchi, 1989, Science 244:1288–1292 and Section 5.14 infra) can be carried out to reduce or destroy endogenous D2-2 function, in order to decrease cell proliferation. Suitable methods, modes of administration and compositions, that can be used to inhibit D2-2 function are described in Sections 5.8.2 through 5.8.2.1.2, above.

In an embodiment of the invention, a Therapeutic that inhibits D2-2 activity is used to treat or prevent hyperproliferative or benign dysproliferative disorders. Specific embodiments are directed to treatment or prevention of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

5.9.2.1. ANTISENSE REGULATION OF D2-2 EXPRESSION

In a specific embodiment, D2-2 function is inhibited by use of D2-2 antisense nucleic acids. The present invention provides the therapeutic or prophylactic use of nucleic acids of at least six nucleotides that are antisense to a gene or cDNA encoding D2-2 or a portion thereof. A D2-2 "antisense" nucleic acid as used herein refers to a nucleic acid capable of hybridizing to a portion of a D2-2 RNA (preferably mRNA) by virtue of some sequence complementarity. The antisense nucleic acid may be complementary to a coding and/or noncoding region of a D2-2 mRNA. Such antisense nucleic acids have utility as Therapeutics that inhibits D2-2 function, and can be used in the treatment or prevention of disorders as described supra in Section 5.8.2 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the D2-2 antisense nucleic acids provided by the instant invention can be used to prevent tumors or other forms of aberrant cell proliferation.

The invention further provides pharmaceutical compositions comprising an effective amount of the D2-2 antisense nucleic acids of the invention in a pharmaceutically acceptable carrier, as described infra.

In another embodiment, the invention is directed to methods for inhibiting the expression of a D2-2 nucleic acid sequence in a prokaryotic or eukaryotic cell comprising providing the cell with an effective amount of a composition comprising an D2-2 antisense nucleic acid of the invention.

D2-2 antisense nucleic acids and their uses are described in detail below.

5.9.2.1.1. D2-2 ANTISENSE NUCLEIC ACIDS

The D2-2 antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a D2-2 antisense oligonucleotide is provided, preferably of single-stranded DNA. The oligonucleotide may be modified at any position on its structure with substituents generally known in the art.

The D2-2 antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the D2-2 antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analog (Inoue et al., 1987, FEBS Lett. 215:327–330).

In an alternative embodiment, the D2-2 antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the D2-2 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the D2-2 antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a D2-2 gene, preferably a human D2-2 gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded D2-2 antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a D2-2 RNA it may contain and still form a stable duplex (or triplex, as the case may be). One skilled in the art can ascertain a tolerable degree of mismatch by use of standard procedures to determine the melting point of the hybridized complex.

5.9.2.1.2. THERAPEUTIC USE OF D2-2 ANTISENSE NUCLEIC ACIDS

The D2-2 antisense nucleic acids can be used to treat (or prevent) disorders of a cell type that expresses, or preferably overexpresses, D2-2. In a specific embodiment, such a disorder is a growth deficiency. In a preferred embodiment, a single-stranded DNA antisense D2-2 oligonucleotide is used.

Cell types which express or overexpress D2-2 RNA can be identified by various methods known in the art. Such methods include but are not limited to hybridization with a D2-2-specific nucleic acid (e.g. by Northern hybridization, dot blot hybridization, in situ hybridization), observing the ability of RNA from the cell type to be translated in vitro into D2-2, immunoassay, etc. In a preferred aspect, primary tissue from a patient can be assayed for D2-2 expression prior to treatment, e.g., by immunocytochemistry or in situ hybridization.

Pharmaceutical compositions of the invention (see Section 5.10), comprising an effective amount of a D2-2 antisense nucleic acid in a pharmaceutically acceptable carrier, can be administered to a patient having a disease or disorder which is of a type that expresses or overexpresses D2-2 RNA or protein.

The amount of D2-2 antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising D2-2 antisense nucleic acids are administered via liposomes, microparticles, or microcapsules. In various embodiments of the invention, it may be useful to use such compositions to achieve sustained release of the D2-2 antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

Additional methods that can be adapted for use to deliver a D2-2 antisense nucleic acid are described in Section 5.9.1.4.

5.10. DEMONSTRATION OF THERAPEUTIC OR PROPHYLACTIC UTILITY

The Therapeutics of the invention are preferably tested in vitro, and then in vivo for the desired therapeutic or prophylactic activity, prior to use in humans.

For example, in vitro assays which can be used to determine whether administration of a specific Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.9.1 through 5.9.3 supra.

In another specific embodiment, a Therapeutic is indicated for use in treating cell injury or a degenerative disorder (see Section 5.8.2) which exhibits in vitro promotion of growth/proliferation of cells of the affected patient type. Regarding nervous system disorders, see also Section 5.8.2.1 for assays that can be used.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.11. THERAPEUTIC/PROPHYLACTIC ADMINISTRATION AND COMPOSITIONS

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described in Sections 5.9.1.4 and 5.9.2.2 above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In addition, it may be desirable to introduce a Therapeutic of the invention into the central nervous system by any suitable route, including, but not limited to intraventricular and intrathecal injection. Intraventricular injection may be facilitated by an intraventricular catheter, for example, attached to a reservoir, such as an Ommaya reservoir. Agents which enhance the delivery of chemotherapeutics to brain tumors, such as agonists which activate specific receptors on endothelial cells which regulate permeability, including, e.g., bradykinin agonists (see, e.g., Elliott, et al., 1996, Cancer Research 56:3998–4005) tumor angiogenesis factors (Cserr and Knopf, 1992, Immunol Today 12:507–512) etc. can be used in formulations and methods of administration when the Therapeutic is intended for delivery to a tumor of the central nervous system.

In a specific embodiment, injection into spinal fluid, and/or procedures utilizing an Ommaya reservoir, can be used to introduce a therapeutic of the invention such as an anti-D2-2 antibody, e.g. a bispecific anti-D2-2 antibody, directly into the central nervous system for immunotherapy of a tumor.

In yet another specific embodiment, an anti-D2-2 antibody, e.g. a bispecific anti-D2-2 antibody, is employed as a Therapeutic in an immunotherapeutic treatment of a non-brain tumor and is infused into a recipient intravenously.

Immune cells, e.g. dendritic cells or cytotoxic T-cells, can cross the blood-brain barrier and have access to brain tissue, especially in the presence of tumor angiogenesis factors (Cserr and Knopf, 1992, Immunol. Today, 12:507–512). In a preferred embodiment, activated dendritic cells (HLA-matched to the recipient) (see generally, Tjoa et al., 1996, Prostate 28: 65–69) that have been exposed to a D2-2 protein, analog or derivative thereof are infused into a recipient under conditions that permit their crossing the blood-brain barrier, e.g. in the presence of tumor angiogenesis factors. In another preferred embodiment, activated cytotoxic T-cells (HLA-matched to the recipient) (see generally, Tjoa et al., 1996, Prostate 28: 65–69) that have been exposed ex vivo (i.e. in vitro) to a D2-2 protein, analog, or derivative thereof are infused into a recipient under conditions that permit their crossing the blood-brain barrier.

In yet another specific embodiment, a Therapeutic of the invention; e.g., activated dendritic cells that have been exposed to a D2-2 protein, analog or derivative thereof, or activated cytotoxic T-cells that have been exposed ex vivo dendritic cells that have been exposed to a D2-2 protein, analog, or derivative thereof, is administered for the treatment of a non-brain tumor.

Pulmonary administration of a Therapeutic can also be employed, e.g., by use of an inhaler or nebulizer, and formulation with an aerosolizing agent.

In a specific embodiment, it may be desirable to administer the Therapeutic of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, 1990 Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.) In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985 Science 228:190; During et al., 1989 Ann. Neurol. 25:351; Howard et al., 1989 J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.11.1. TREATMENT AND PREVENTION OF HYPOPROLIFERATIVE DISORDERS

Diseases and disorders involving decreased cell proliferation or in which cell proliferation is desired for treatment or prevention, and that can be treated or prevented by promoting D2-2 function, include but are not limited to degenerative disorders, growth deficiencies, hypoproliferative disorders, physical trauma, lesions, and wounds; for example, to promote wound healing, or to promote regeneration in degenerated, lesioned or injured tissues, etc. In a specific embodiment, nervous system disorders are treated. In another specific embodiment, a disorder that is not of the nervous system is treated.

Lesions which may be treated according to the present invention include but are not limited to the following lesions:

(i) traumatic lesions, including lesions caused by physical injury or associated with surgery;

(ii) ischemic lesions, in which a lack of oxygen results in cell injury or death, e.g., myocardial or cerebral infarction or ischemia, or spinal cord infarction or ischemia;

(iii) malignant lesions, in which cells are destroyed or injured by malignant tissue;

(iv) infectious lesions, in which tissue is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which tissue is destroyed or injured as a result of a degenerative process, including but not limited to nervous system degeneration associated with Parkinson's disease, Alzheimer's disease, Huntington's chorea, or amyotrophic lateral sclerosis;

(vi) lesions associated with nutritional diseases or disorders, in which tissue is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) lesions associated with systemic diseases including but not limited to diabetes or systemic lupus erythematosus;

(viii) lesions caused by toxic substances including alcohol, lead, or other toxins; and (ix) demyelinated lesions of the nervous system, in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Nervous system lesions which may be treated in a patient (including human and non-human mammalian patients) according to the invention include but are not limited to the lesions of either the central (including spinal cord, brain) or peripheral nervous systems.

Therapeutics which are useful according to this embodiment of the invention for treatment of a disorder may be selected by testing for biological activity in promoting the survival or differentiation of cells (see also Section 5.9). For example, in a specific embodiment relating to therapy of the nervous system, a Therapeutic which elicits one of the following effects may be useful according to the invention:

(i) increased sprouting of neurons in culture or in vivo;

(ii) increased production of a neuron-associated molecule in culture or in vivo, e.g., choline acetyltransferase or acetylcholinesterase with respect to motor neurons; or (iii) decreased symptoms of neuron dysfunction in vivo. Such effects may be measured by any method known in the art. In preferred, non-limiting embodiments, increased sprouting of neurons may be detected by methods set forth in Pestronk et al. (1980, Exp. Neurol. 70:65–82) or Brown et al. (1981, Ann. Rev. Neurosci. 4:17–42); and increased production of neuron-associated molecules may be mea-

5.12. ADDITIONAL USE OF INCREASED D2-2 FUNCTION TO PROMOTE INCREASED GROWTH

Promotion of D2-2 function (e.g., by administering a compound that promotes D2-2 function as described in Sections 5.8.2 through 5.8.2.1.2 above), has utility that is not limited to therapeutic or prophylactic applications. For example, D2-2 function can be promoted in order to increase growth of animals (e.g., cows, horses, pigs, goats, deer, chickens) and plants (particularly edible plants, e.g., tomatoes, melons, lettuce, carrots, potatoes, and other vegetables), particularly those that are food or material sources. In an embodiment in which a D2-2 nucleic acid is under the control of a tissue-specific promoter, the invention can be used in plants or animals to increase growth where desired (e.g., in the fruit or muscle). For example, a D2-2 nucleic acid under the control of a temperature-sensitive promoter can be administered to a plant or animal, and the desired portion of the (or the entire) plant or animal can be subjected to heat in order to induce D2-2 nucleic acid production, resulting in increased D2-2 expression, and resulting cell proliferation. Methods to make plants recombinant are commonly known in the art and can be used. Regarding methods of plant transformation (e.g., for transformation with a D2-2 antisense nucleic acid), see e.g., Valvekens et al., 1988, Proc. Natl. Acad. Sci. USA 85:5536–5540. Regarding methods of targeted gene inactivation in plants (e.g., to inactivate D2-2), see e.g., Miao and Lam, 1995, The Plant J. 7:359–365.

Promotion of D2-2 function can also have uses in vitro, e.g., to expand cells in vitro, including but not limited to stem cells, progenitor cells, muscle cells, fibroblasts, liver cells, etc., e.g., to grow cells/tissue in vitro prior to administration to a patient (preferably a patient from which the cells were derived), etc.

5.13. SCREENING FOR D2-2 AGONISTS AND ANTAGONISTS

D2-2 nucleic acids, proteins, and derivatives also have uses in screening assays to detect molecules that specifically bind to D2-2 nucleic acids, proteins, or derivatives and thus have potential use as agonists or antagonists of D2-2, in particular, molecules that thus affect cell proliferation. In a preferred embodiment, such assays are performed to screen for molecules with potential utility as anti-cancer drugs or lead compounds for drug development. The invention thus provides assays to detect molecules that specifically bind to D2-2 nucleic acids, proteins, or derivatives. For example, recombinant cells expressing D2-2 nucleic acids can be used to recombinantly produce D2-2 proteins in these assays, to screen for molecules that bind to a D2-2 protein. Molecules (e.g., putative binding partners of D2-2) are contacted with the D2-2 protein (or fragment thereof) under conditions conducive to binding, and then molecules that specifically bind to the D2-2 protein are identified. Similar methods can be used to screen for molecules that bind to D2-2 derivatives or nucleic acids. Methods that can be used to carry out the foregoing are commonly known in the art.

By way of example, diversity libraries, such as random or combinatorial peptide or nonpeptide libraries can be screened for molecules that specifically bind to D2-2. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R.B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated August 18, 1994.

In vitro translation-based libraries include but are not limited to those described in PCT Publication No. WO 91/05058 dated April 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318.

In a specific embodiment, screening can be conducted out by contacting the library members with a D2-2 protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to a D2-2 protein or derivative.

5.14. ANIMAL MODELS

The invention also provides animal models. In one embodiment, animal models for diseases and disorders involving cell hypoproliferation (e.g., as described in Section 5.8.1) are provided. Such an animal can be initially produced by promoting homologous recombination between a D2-2 gene in its chromosome and an exogenous D2-2 gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated D2-2 gene, such that homologous recombination occurs, followed by injecting the ES cells into a blastocyst, and implanting the blastocyst into a foster mother, followed by the birth of the chimeric animal ("knockout animal") in which a D2-2 gene has been inactivated (see Capecchi, 1989, Science 244:1288–1292). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving cell hypoproliferation. Such animals can be used to screen for or test molecules for the ability to promote proliferation and thus treat or prevent such diseases and disorders.

In a different embodiment of the invention, transgenic animals that have incorporated and express a functional D2-2 gene have use as animal models of diseases and disorders involving cell hyperproliferation or malignancy. Such animals are expected to develop or be predisposed to developing diseases or disorders involving cell hyperproliferation (e.g., malignancy) and thus can have use as animal models of such diseases and disorders, e.g., to screen for or test molecules (e.g., potential anti-cancer therapeutics) for the ability to inhibit overproliferation (e.g., tumor formation) and thus treat or prevent such diseases or disorders.

6. EXAMPLE: ISOLATION AND CHARACTERIZATION OF THE D2-2 GENE FROM HUMAN GLIOBLASTOMA MULTIFORME TUMOR TISSUE

Specific markers are needed to recognize and diagnose brain tumors in early stages of tumorigenesis. This example describes the isolation of a novel gene, D2-2, that is over-expressed in glioblastoma multiforme tissue (GMT) and normal fetal brain tissue as compared to normal adult brain tissue (NBT).

6.1. MATERIALS AND METHODS

6.1.1. HUMAN TISSUES AND CELL LINES

Various tumor samples of brain and non-brain tumors were procured from the tissue bank maintained by Pacific Northwest Cancer Foundation, Northwest Hospital and from resources at the Mayo Clinic in Minnesota. Brain tumor cell lines CCF-STTG1 (astrocytoma grade IV), SW 1783 (astrocytoma grade III), IMR-32 (neuroblastoma), D283 Med (medulloblastoma), Hs 683 (glioma), PFSK-1 (primitive neuroectodermal tumor) and DBTRG-05MG (glioblastoma multiforme) cell lines were purchased from ATCC (American Type Culture Collection, Rockville, Md.). Fetal normal human astrocytes (FNHA) were purchased from Clonetics (San Diego, Calif.). All the cell lines were cultured under the conditions recommended by ATCC or Clonetics.

6.1.2. DIFFERENTIAL DISPLAY—POLYMERASE CHAIN REACTION (DD-PCR)

The D2-2 gene was isolated using the Differential Display—Polymerase Chain Reaction (DD-PCR) technique. DD-15 PCR is a modified PCR technique first developed in 1992 (Liang et al., 1992, Science, 257:967–971; and Liang et al., 1992, Cancer Res., 52:6966–6968). This technique is much more sensitive and reproducible than previously documented techniques of differential hybridization and subtractive library construction. DD-PCR technique has been modified and improved to increase PCR specificity and efficiency (Hadman et al., 1995 Anal. Biochem., 226:383–386; Bauer et al., 1993 Nucleic Acids Res., 21:4272–4280).

Differentially expressed genes from NBT (Normal brain tissue) and GMT (Glioblastoma Multiforme Tissue) were isolated and cloned using the protocol of Hadman et al. supra. NBT and GMT were obtained from the same region of the brain. Total RNA was isolated using the GITC/CsCl$_2$ protocol described previously by Sambrook et al., 1989 Molecular Cloning A Laboratory Manual, 2nd ed, Cold Spring Harbor, N.Y.: Cold Spring Harbor Laboratory. Five µg of total RNA was treated with DNaseI (Amersham, Arlington Heights, Ill.) (2u/µl) for 30 minutes at 37° C. RNA was then extracted and precipitated using 3M sodium acetate. First strand cDNA synthesis was then carried out using the Advantage 1st Strand cDNA synthesis kit from Clontech (Palo Alto, Calif.) and BT3-2 primer (5'T(T) 18NG3'). Approximately 125 ng of first strand cDNA synthesis product was used for carrying out the PCR reaction. DD-PCR reaction was carried out using ($\gamma$P$^{32}$)end labelled BT-2 primer and BT-8 (5'NTACTGATCCATGACA3') (SEQ ID NO: 3), BT-10 (5'NGCTGCTCTCATACT3') (SEQ ID NO: 4), or BT-12 (5'NTGATCTAAGGCACATA3') (SEQ ID NO: 5) primers using cDNA from NBT or GMT tissue in duplicate, and using the conditions of Hadman et al., supra. PCR products were then electrophoresed on a 6% sequencing gel. The bands that showed differential expression were then cut out and DNA was eluted. PCR was then carried as done for DD-PCR conditions using appropriate primers. PCR product was then cloned into PCRII vector from Invitrogen (San Diego, Calif.). Positive clones were screened by PCR and sequenced using the Sequenase version 2.0 sequencing kit (Amersham/USB, Arlington Heights, Ill.).

6.1.3. GENE-SPECIFIC REVERSE TRANSCRIPTION POLYMERASE CHAIN REACTION (RT-PCR)

To confirm the differential expression of clones isolated by DD-PCR, a RT-PCR technique (Ikonomov et al., 1996, Biotechniques, 20:1030–1042) was used. In brief 5 µg of total RNA was treated with DNaseI and first strand synthesis was carried out under the same conditions as described previously. First strand cDNA was used as template to carry out PCR using primers BT-41 (5'CTCAGTGTTAACGGATAAT3') (SEQ ID NO: 8) and BT-42 (5'TGTTGAGAAGAGTACATCTT3') (SEQ ID NO: 9) that were specific for D2-2. As a control clone, D1-2, which is expressed in both NBT and GMT at the same level, was used as an internal control.

PCR for D1-2 was carried out using BT-59 (5'CGGAGCAATATGAAATGATCT3') (SEQ ID NO: 10) and BT-60 (5'GCAAATACAGCTCCTATTG3') (SEQ ID NO: 11). PCR was carried out using a Gene Amp PCR kit (Perkin-Elmer, Branchburg, Ill.) under the following conditions: 4 µl of dNTP mix, 2 µl (100 ng/µl) each of D1-2 or D2-2 specific primers, 4 µl of 25 mM MgCl$_2$, 125 ng of cDNA template and 5 units of Amplitaq DNA polymerase. PCR conditions were as follows: 94° C., 50° C. and 72° C. for 1 minute each for 35 cycles. PCR product was then run on a 2% agarose gel. DNA was transferred on to MSI Magnacharge membrane using standard Southern Blotting conditions known in the art (Sambrook et al., supra). Hybridization was done at 42° C. using D1-2 and D2-2 specific probes. D1-2 and D2-2 specific probes were prepared by the multiprime labelling (using an Amersham Megaprime Labelling Kit, Arlington Heights, Ill.) of D2-2 specific primers BT-66 (5'CCAAACTGGACATCAAGG AATTGCTACACAGAAGAACCACCATCCAGGATAGA A3') (SEQ ID NO: 12) or D1-2 specific primer BT-69 (5'TAGGCCTGACTGGCATTGTATTAGCAAACTCATC ACTAGA3') (SEQ ID NO: 13). These primers are internal to the primers used for PCR and they do not carry any of the primer sequences used in the PCR.

Primer sequences were checked for homologous sequences using the DNA BLAST program prior to usage. Quantitation of the signal on the Southern blot was carried out using the ImageQuaNT™ program and a Molecular Dynamics Phosphor Imager (Sunnyvale, Calif.). This protocol was also used to quantitate expression of D2-2 or D1-2 in brain tumor cell lines, FNHA and tumor tissues.

6.1.4. CLONING AND SEQUENCING OF D2-2

DD-PCR product for clone D2-2 was about 250 bases long. It had 100% homology to a partial DNA sequence (1.0 kb) in the TIGR (The Institute for Genome Research, Rockville, Md.) database which has no known function or homology to other sequences in the database. A partial fragment of D2-2 (an EcoRI and XbaI 750 bp fragment) was used to screen a human brain library from Stratagene (La Jolla, Calif.). One positive clone of 2.0 Kb insert size was isolated. Both strands were sequenced by Sequetech Corporation (Mountain View, Calif.).

6.1.5. NORTHERN BLOT ANALYSIS

To investigate the expression of D2-2 in different normal tissues, Multiple Tissue Blots (MTB) from Clontech (Palo Alto, Calif.) were used. These blots contained 2 $\mu$g of pure PolyA mRNA blotted. MTBs were prehybridized in express hybridization buffer solution for 3–4 hours. Hybridization was done with multiprime-labelled 750 bp D2-2 probe. After autoradiographic exposure, the probe was washed from the blot and then hybridized with human $\beta$ actin probe. Quantitation of expression of D2-2 and $\beta$ actin was achieved using the ImageQuaNT™ program of the Molecular Dynamic Phosphor Imager (Sunnyvale, Calif.).

6.1.6. DOT BLOT ANALYSIS

To study the expression of D2-2 in fetal and adult tissues, Master Blot from Clontech (Palo Alto, Calif.) was used. The Master Blot contained 200 ng of pure polyA RNA blotted onto the membrane. Prehybridization and hybridization was conducted with the 750 bp D2-2 probe as described supra for Northern Blot analysis. To normalize the RNA, the blot was hybridized with human ubiquitin probe. Quantitation of the signal was achieved using the Molecular Dynamic Phosphor Imager.

6.1.7. QUANTITATION OF NORTHERN AND SOUTHERN BLOTS

Quantitation of Northern and Southern blots was performed using the ImageQuaNT™ volume quantitation program from the Molecular Dynamics Phosphor Imager (Sunnyvale, Calif.). Volume quantitation calculates the volume under the surface created by a 3-D plot of pixel locations and pixel values. The volume (i.e. the integrated intensity of all the pixels in the spot excluding the background) of the D2-2 bands in Northern or Southern blots was quantitated. These pixel values were then normalized with pixel values in the bands of housekeeping genes (D1-2 or $\beta$ -actin), and are referred to as "relative expression" in the descriptions of the figures in Section 4, supra. The subjective terms of "low," "medium," and "high" relative expression are based on D2-2 expression in normal brain as being low and in tumor brain tissue as being high.

6.2. RESULTS

6.2.1. ISOLATION OF DIFFERENTIALLY EXPRESSED GENES USING DD-PCR

The modified DD-PCR technique was used to isolate genes that are differentially expressed either in NBT or GMT as described in Section 6.1.2, supra. Using one 3' primer and three 5' primers, DD-PCR was performed on GMT and NBT. Nineteen bands were isolated that showed differential expression either in GMT or NBT. Fourteen of these bands were expressed at higher levels in GMT and four were is expressed at higher levels in NBT. All of these bands were isolated, and DNA was eluted, reamplified and cloned into the PCRII vector from Invitrogen (San Diego, Calif.).

Sequence analyses of these clones indicated that the majority of these genes had no homology to known sequences in the National Sequence database (The National Institutes of Health (NIH), Bethesda, Md.). Clone D2-2 was characterized in detail; it appears to be unique because it shows high expression in GMT but not in NBT (see FIG. 1A and 1B).

Using the gene-specific RT-PCR technique, as described, supra, in Section 6.1.3, D2-2 was found to be overexpressed 55-fold in GMT and 8.5-fold in meningioma tumor tissue (MTT) as compared to NBT (FIGS. 2A–C). D2-2 was detected at very low levels in a B cell lymphoma tumor sample. D1-2, a gene that was isolated from the same DD-PCR and is expressed consistently in normal and tumor samples, was used as an internal control. The results presented in FIGS. 2A–C indicate that D2-2 is differentially expressed in GMT and NBT.

To demonstrate that this gene-specific RT-PCR is quantitative and well within the linear range, RT-PCR was performed using D1-2 and D2-2 specific primers, and with increasing numbers of cycles. Results obtained in this experiment demonstrate that gene specific RT-PCR is quantitative and well within the linear range (data not shown).

6.2.2. SEQUENCE ANALYSIS OF CLONE D2-2

The D2-2 clone that was isolated by DD-PCR is only 250 base pairs in length and it has a long polyA tail. This clearly indicates that the D2-2 sequence is at the 3' end of the gene. No known identical sequences for D2-2 were found in the National database (NIH, Bethesda, Md.). Conversely, sequence homology analysis of D2-2 with the TIGR (The Institute for Genome Research, Rockville, Md.) database indicated that there was 100% homology to a 1.0 Kb partial cDNA (SEQ ID NO: 14) with no known function, cloned from brain or prostate adenocarcinoma tissue (Gleason score of 9). Since the length of D2-2 isolated from DD-PCR is 250 bp, the rest of the TIGR clone was searched for homologous sequences in the National database (NIH, Bethesda, Md.). No significant homology was found.

To isolate the full length of D2-2 clone, a human fetal brain library was screened. Using this method, one clone was isolated that was about 2.0 Kb in size (SEQ ID NO: 1).

This EcoRI-XhoI fragment was sequenced from both the strands and the nucleotide sequence is shown in FIG. 3. Sequence analysis indicated that it has a small ORF (open reading frame) and the deduced amino acid sequence is also shown in FIG. 3. Protein homology analysis of the partial amino acid sequence also demonstrated that there are three HLA-A2+ motifs as represented by SEQ ID NO: 15 (amino acids 8–16), SEQ ID NO: 17 (amino acids 27–35), and SEQ ID NO: 19 (amino acids 56–63). The 80 amino acids of the presently taught ORF have no other homology to known proteins in the National database. Except for the presence of 80 amino acids, the majority of the fragment has a 3' untranslated sequence. This indicates that D2-2 is a novel protein. Analysis of the 3' UTR (untranslated region) indicated that there are small stretches of Alu repeat sequences. This analysis demonstrates that D2-2 is a novel gene.

6.2.3. EXPRESSION OF D2-2 IN TUMOR TISSUES

The expression of D2-2 was examined in other tissue samples obtained from the Northwest Hospital Tissue Bank. RT-PCR of D2-2 was performed as described in Section 6.1.3 supra. D1-2 was used as a control. Results are shown in FIGS. 4A–C.

As shown in FIGS. 4A–C, high levels of expression of D2-2 are observed in glioblastoma, recurrent glioma, colon cancer metastatic to brain, prostate adenocarcinoma (Gleason score of 9) tumors, and the LNCaP (prostate cancer) cell line. Moderate to low levels of D2-2 expression were observed in two cases of meningiomas, a diffuse malignant lymphoma of the B cell type and a breast ductal carcinoma as compared to normal brain. These results confirm that overexpression of D2-2 is not confined to brain tumor tissues.

6.2.4. EXPRESSION OF D2-2 IN BRAIN TUMOR CELL LINES AND NORMAL HUMAN (FETAL) ASTROCYTES

The expression of D2-2 in cell lines derived from different human brain tumors and normal human astrocytes (fetal) was investigated by growing human brain tumor cell lines (glioblastoma, astrocytoma grade III, astrocytoma grade IV, glioma, medulloblastoma, neuroectodermal, neuroblastoma) to 80% confluency. PCR and Southern blot analysis were performed as described in Section 6.1.3., supra. As shown in FIGS. 5A—C, D2-2 is expressed at very high levels in glioblastoma, astrocytoma grade IV, glioma and FNHA. Moderate levels were expressed in neuroectodermal and medulloblastoma brain tumor. These results showed that D2-2 is expressed at high levels in the majority of the brain tumor cell lines investigated.

6.2.5. EXPRESSION OF D2-2 IN HUMAN TUMOR CELL LINES

Using Northern Blot analysis, expression of D2-2 was studied in several tumor cell lines as described in Section 6.1.5. As shown in FIG. 6A-C, MOLT lymphoblastic leukemia, SW480 colorectal adenocarcinoma, A549 lung carcinoma, HL-60 promyelocytic leukemia, S3 HeLa cells, K-562 chronic myelogenous leukemia and G361 melanoma showed high expression, and Burkitt's lymphoma Raji showed low expression of D2-2 as compare to NBT. These results demonstrate that D2-2 is overexpressed in the majority of the tumor cell lines investigated.

6.2.6. EXPRESSION OF D2-2 IN DIFFERENT REGIONS OF NORMAL HUMAN BRAIN

To understand the function of D2-2 in the brain, its expression in different regions of the brain was examined. Eight different regions of the normal human brain were studied as described in Section 6.1.5. As shown in FIGS. 7A–C, D2-2 is expressed at high levels in the frontal lobe, occipital lobe and cerebellum.

6.2.7. EXPRESSION OF D2-2 IN NORMAL HUMAN TISSUE

To determine whether D2-2 expression was confined to the brain, the expression of D2-2 in other normal human tissues was examined using Northern blot analysis as described in Section 6.1.5, supra. As shown in FIGS. 8A–C, D2-2 is expressed at high levels in thyroid, and at moderate levels in pancreas, adrenal cortex, testis, thymus, small intestine, stomach and fetal liver. The remaining tissues expressed D2-2 minimally. It is interesting to note that D2-2 was expressed in much higher levels in tissues of the endocrine system.

To investigate whether D2-2 has a role in the immune system, its expression was studied in different organs from the immune system. As shown in FIGS. 8A–C, expression for D2-2 is highest in thymus and fetal liver as compared to lymph node, appendix, peripheral blood leukocytes or bone marrow. The significance of high level of D2-2 expression in normal tissue of selective organs is not known at present.

6.2.8. EXPRESSION OF D2-2 DURING DEVELOPMENT

A number of oncogenes that are over expressed in tumors, e.g., jun and fos, are also shown to be very highly expressed during early development hence they are termed onco-fetal proteins (Angel and Karin, 1991 Biochem. Biophys. Acta, 1072: 129–157). To investigate whether D2-2 also shows a similar expression pattern, the expression of D2-2 was studied in seven fetal (20 weeks) and adult tissues using dot blot analysis as described in section 6.1.6, supra.

As shown in FIG. 9, D2-2 is expressed at very high levels in fetal brain and heart as compared to adult brain and heart. Conversely, such a dramatic difference in expression has not been observed with kidney, liver, spleen, lung or thymus. These results indicate that D2-2 may be involved in some function during early development. Although not intending to be limited to any particular explanation, the inventors propose that D2-2 may be an onco-fetal protein.

6.2.9. EXPRESSION OF D2-2 IN CULTURE MEDIUM CONTAINING OR LACKING SERUM

Several oncogenes such as jun and fos are expressed at high levels when cells are proliferating rapidly in a serum-containing media (Angel and Karin, 1991 Biochem. Biophys. Acta, 1072: 129–157). If cells are starved for serum for 48 hours or longer, the majority of cells enter $G_0/G_1$ phase of the cell cycle. Not only will these cells will stop proliferation, but expression of these oncogenes also decreases several fold.

The expression of D2-2 in several brain tumor cell lines in culture media containing or lacking serum was studied. The results showed that expression of D2-2 decreases in cells (neuroectodermal, glioblastoma and FNHA) that are starved for serum for 72 hours (data not shown).

Onco-fetal proteins show high expression not only during early development but also in several different tumor types. D2-2 is expressed at very high levels in the brain and heart of 20 week old fetus, but its expression drops to low level in adults. This indicates that D2-2 plays an important role during early brain and heart development.

6.3. DISCUSSION

D2-2 is overexpressed in glioblastoma multiforme and cell lines derived from other types of brain tumors. It has high expression not only in the GMT tissue from which it was isolated, but also in the majority of non-brain tumor cell lines and tissues examined. With the exception of the promyelocytic leukemia HL-60 and Burkitt's lymphoma Raji cell lines, the majority of tumor cell lines derived from non-brain tissues showed high expression of D2-2. In addition, D2-2 is expressed at high levels in other tumor tissues such as prostate adenocarcinoma (Gleason score of 9), breast ductal carcinoma and LNCaP (prostate tumor cell line) cell lines. This demonstrates that D2-2 is a gene with high expression in a variety of tumors, besides brain tumors.

D2-2 was detected at very low levels in two brain tumor cell lines, i.e., grade III astrocytoma and neuroblastoma cell lines. The reason for this low expression is not known at present, however, it is envisaged that such expression patterns can be used for differential detection or diagnosis of brain tumors such as, but not limited to, glioblastoma, astrocytoma, glioma, neuroectodermal, and medulloblastomas.

In addition to all the applications detailed hereinabove, the present invention has utility in elucidating the process of tumorigenesis for early detection of brain tumors, including but not limited to highly malignant brain tumors, and provides better strategies for effective treatment of brain tumors.

7. DEPOSIT OF MICROORGANISM

E. coli designated NWB-D2-2 containing plasmid D2-2, containing an EcoRI-XhoI 2.0 Kb fragment was deposited on Nov. 5, 1996 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 98246.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

---

What is claimed is:

1. An isolated nucleic acid comprising a nucleotide sequence encoding a D2-2 protein, said nucleic acid having the sequence of SEQ ID NO: 1.

2. An isolated nucleic acid comprising a nucleotide sequence complementary to the nucleotide sequence of claim 1.

3. An isolated nucleic acid comprising a 2 Kb EcoRI-XhoI fragment encoding D2-2 identical to that obtained from *Escherichia coli* NWB-D2-2 as deposited with the ATCC and assigned accession number 98246.

4. An isolated nucleic acid having a sequence complementary to the isolated nucleic acid of claim 3.

5. An isolated nucleic acid having a sequence complementary to a DNA having a sequence consisting of the coding region of SEQ ID NO. 1.

6. An isolated nucleic acid having a sequence consisting of SEQ ID NO: 6.

7. An isolated nucleic acid comprising a fragment of a nucleic acid, wherein said fragment consists of at least 15 contiguous nucleotides of SEQ ID NO:6.

8. An isolated nucleic acid comprising a nucleotide sequence encoding a protein, said protein comprising amino acid sequence of SEQ ID NO:7.

9. A recombinant cell containing the nucleic acid of claim 1.

10. A recombinant cell containing the nucleic acid of claim 8.

11. The isolated nucleic acid of claim 7 consisting of at least 25 contiguous nucleotides.

12. The isolated nucleic acid of claim 7 consisting of at least 50 contiguous nucleotides.

13. The isolated nucleic acid of claim 7 consisting of at least 100 contiguous nucleotides.

14. The isolated nucleic acid of claim 7 consisting of at least 200 contiguous nucleotides.

15. An isolated nucleic acid comprising a nucleotide sequence encoding a D2-2 protein, said D2-2 protein having a sequence selected from the group consisting of SEQ ID NO: 15, SEQ ID NO: 17, and SEQ ID NO: 19.

16. An isolated nucleic acid comprising a nucleotide sequence complementary to the nucleotide sequence of claim 15.

* * * * *